US010041971B2

(12) United States Patent
Grinolds et al.

(10) Patent No.: US 10,041,971 B2
(45) Date of Patent: Aug. 7, 2018

(54) NANOSCALE SCANNING SENSORS

(71) Applicant: PRESIDENT AND FELLOWS OF HARVARD COLLEGE, Cambridge, MA (US)

(72) Inventors: Michael S. Grinolds, Somerville, MA (US); Sungkun Hong, Vienna (AT); Patrick Maletinsky, Basel (CH); Amir Yacoby, Newton, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 14/423,123

(22) PCT Filed: Aug. 20, 2013

(86) PCT No.: PCT/US2013/055644
§ 371 (c)(1),
(2) Date: Feb. 21, 2015

(87) PCT Pub. No.: WO2014/051886
PCT Pub. Date: Apr. 3, 2014

(65) Prior Publication Data
US 2015/0253355 A1 Sep. 10, 2015

Related U.S. Application Data

(60) Provisional application No. 61/692,077, filed on Aug. 22, 2012.

(51) Int. Cl.
*G01Q 70/14* (2010.01)
*G01N 21/64* (2006.01)
(Continued)

(52) U.S. Cl.
CPC ........... *G01Q 70/14* (2013.01); *G01N 21/645* (2013.01); *G01N 24/10* (2013.01); *G01Q 60/38* (2013.01);
(Continued)

(58) Field of Classification Search
CPC ......... B82Y 35/00; C30B 29/04; G01R 33/24; G01R 33/022; G01R 33/032;
(Continued)

(56) References Cited

U.S. PATENT DOCUMENTS 5,861,624 A * 1/1999 Alexander ............. B82Y 35/00
850/26
2004/0218441 A1* 11/2004 Schwarzl ...................... 365/202
(Continued)

FOREIGN PATENT DOCUMENTS

WO       2010051580 A1    5/2010
WO    WO 2010051580 A1 *  5/2010

OTHER PUBLICATIONS

Maletinsky et al., "A robust scanning diamond sensor for nanoscale imaging with single nitrogen-vacancy centres" and supplementary information, Apr. 15, 2012, Nature Nanotechnology, vol. 7, No. 5, pp. 320-324, DOI: 10.1038/nnano.2012.50.*
(Continued)

*Primary Examiner* — David Porta
*Assistant Examiner* — Blake Riddick
(74) *Attorney, Agent, or Firm* — Elizabeth Kim Patent Law Offices LLC

(57) ABSTRACT

A sensing probe may be formed of a diamond material comprising one or more spin defects that are configured to emit fluorescent light and are located no more than 50 nm from a sensing surface of the sensing probe. The sensing probe may include an optical outcoupling structure formed by the diamond material and configured to optically guide
(Continued)

the fluorescent light toward an output end of the optical outcoupling structure. An optical detector may detect the fluorescent light that is emitted from the spin defects and that exits through the output end of the optical outcoupling structure after being optically guided therethrough. A mounting system may hold the sensing probe and control a distance between the sensing surface of the sensing probe and a surface of a sample while permitting relative motion between the sensing surface and the sample surface.

10 Claims, 29 Drawing Sheets

(51) Int. Cl.

| | |
|---|---|
| *G01N 24/10* | (2006.01) |
| *G01Q 60/38* | (2010.01) |
| *G01Q 60/54* | (2010.01) |
| *G01R 33/022* | (2006.01) |
| *G01R 33/032* | (2006.01) |
| *G01R 33/12* | (2006.01) |
| *G01R 33/60* | (2006.01) |
| *G01Q 30/02* | (2010.01) |
| *G01Q 60/08* | (2010.01) |
| *G01R 33/32* | (2006.01) |

(52) U.S. Cl.
CPC ............ *G01Q 60/54* (2013.01); *G01R 33/022* (2013.01); *G01R 33/032* (2013.01); *G01R 33/1284* (2013.01); *G01R 33/60* (2013.01); *G01N 2201/10* (2013.01); *G01Q 30/025* (2013.01); *G01Q 60/08* (2013.01); *G01R 33/323* (2013.01)

(58) Field of Classification Search
CPC .. G01R 33/1284; G01R 33/323; G01R 33/60; G01N 21/64; G01N 21/645; G01N 2201/10; G01Q 70/14; G01Q 60/54; G01Q 60/38; G01Q 70/16; G01Q 70/18; G01Q 60/08; G01Q 60/22; G01Q 30/025
USPC ................ 250/484.2, 483.1, 458.1; 423/446; 850/40, 48, 59, 31
See application file for complete search history.

(56) References Cited

U.S. PATENT DOCUMENTS

| | | | |
|---|---|---|---|
| 2005/0223785 A1* | 10/2005 | Watanabe et al. ............. | 73/105 |
| 2009/0233445 A1* | 9/2009 | Lee ........................ | B82Y 15/00 |
| | | | 438/694 |
| 2010/0207622 A1* | 8/2010 | Finkler et al. ................ | 324/248 |
| 2010/0308813 A1* | 12/2010 | Lukin et al. ............... | 324/244.1 |
| 2010/0315079 A1* | 12/2010 | Lukin et al. ............... | 324/244.1 |
| 2010/0329962 A1* | 12/2010 | Twitchen et al. ............. | 423/384 |
| 2011/0163291 A1* | 7/2011 | Scarsbrook .......... | G06N 99/002 |
| | | | 257/9 |
| 2011/0309265 A1* | 12/2011 | Babinec et al. ........... | 250/459.1 |
| 2012/0019242 A1* | 1/2012 | Hollenberg et al. .......... | 324/300 |
| 2012/0051996 A1* | 3/2012 | Scarsbrook et al. .......... | 423/446 |
| 2014/0061510 A1* | 3/2014 | Twitchen ................ | C30B 29/04 |
| | | | 250/492.1 |
| 2014/0191139 A1* | 7/2014 | Englund .......... | G01N 33/48728 |
| | | | 250/459.1 |

OTHER PUBLICATIONS

Taylor et al., "High-sensitivity diamond magnetometer with nanoscale resolution", May 8, 2008, arxiv.org, pp. 1-29.*
Rondin et al., "Nanoscale magnetic field mapping with a single spin scanning probe magnetometer", Apr. 12, 2012, Applied Physics Letters, vol. 100, No. 15, pp. 153118-1 to 153118-4.*
Le Sage et al., "Efficient photon detection from color centers in a diamond optical waveguide", Mar. 23, 2012, Physical Review B, vol. 85, No. 12, pp. 121202-1 to 121202-4.*
Balasubrananian et al., "Nanoscale imaging magnetometry with diamond spins under ambient conditions" and supplemental information, Oct. 2, 2008, Nature, vol. 455, pp. 648-651, doi:10.1038/nature07278.*
Hemmer, P., 2009, "NV Diamond Micro-Magnetometer Baseline Studies", US Defense Technical Information Center.*
Hahn, E.L., 1950, "Spin Echoes", Phys. Rev. 80 (4), pp. 580-594.*
P. Maletinsky et al, "A robust scanning diamond sensor for nanoscale imaging with single nitrogen-vacancy centres," Nature Nanotechnology, vol. 7, No. 5, Apr. 15, 2012 (Apr. 15, 2012), pp. 320-324, MacMillan Publishers Limited.
Taylor J M et al, "High-sensitivity diamond magnetometer with nanoscale resolution", Internet Citation, May 8, 2008 (May 8, 2008), pp. 1-29, XP007908377, Retrieved from the Internet: URL:http://arxiv.org/PS_cache/arxiv/pdf/0805/0805.1367v1.pdf.
Rondin L et al, "Nanoscale magnetic field mapping with a single spin scanning probe magnetometer," Applied Physics Letters, vol. 100, No. 15, Apr. 9, 2012 (Apr. 9, 2012), pp. 153118-1, American Institute of Physics.
D. Le Sage et al, "Efficient photon detection from color centers in a diamond optical waveguide," Physical Review B, vol. 85, No. 12, Mar. 23, 2012.
Notification of Transmittal of the International Search Report and Written Opinion of the International Searching Authority, or the Declaration, for PCT/US2013/055644, dated Mar. 11, 2014, 14 pages, International Searching Authority/EPO, Rijswijk, the Netherlands.

* cited by examiner

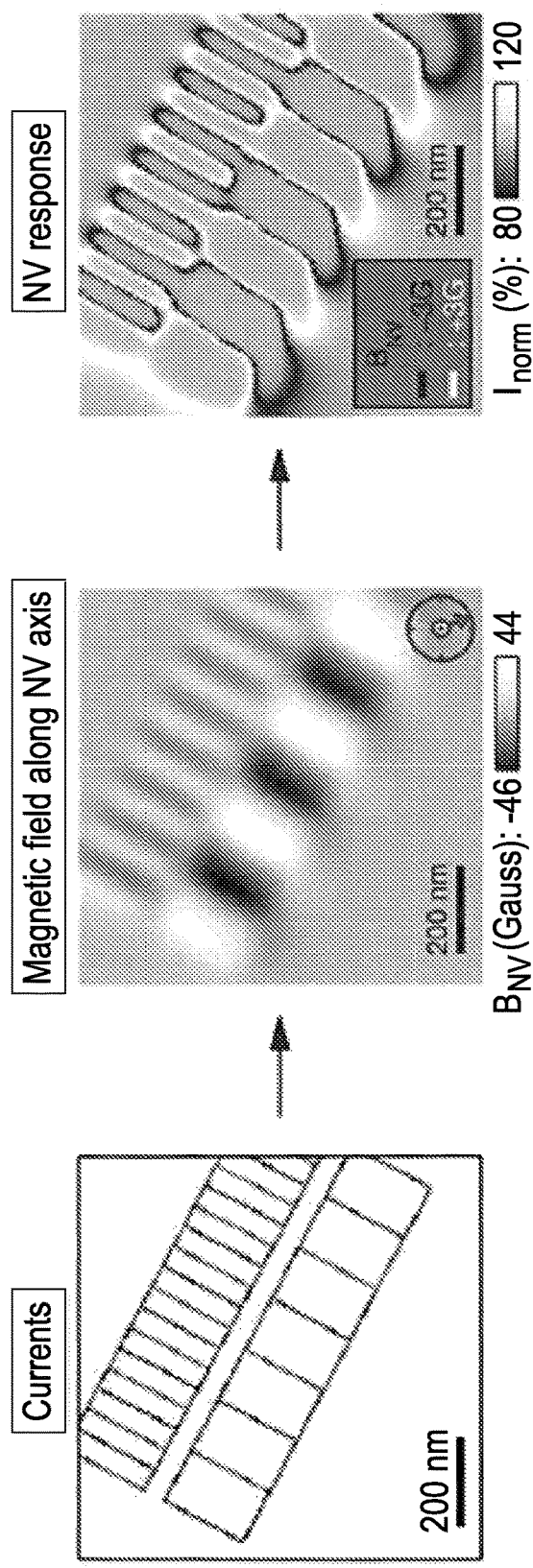

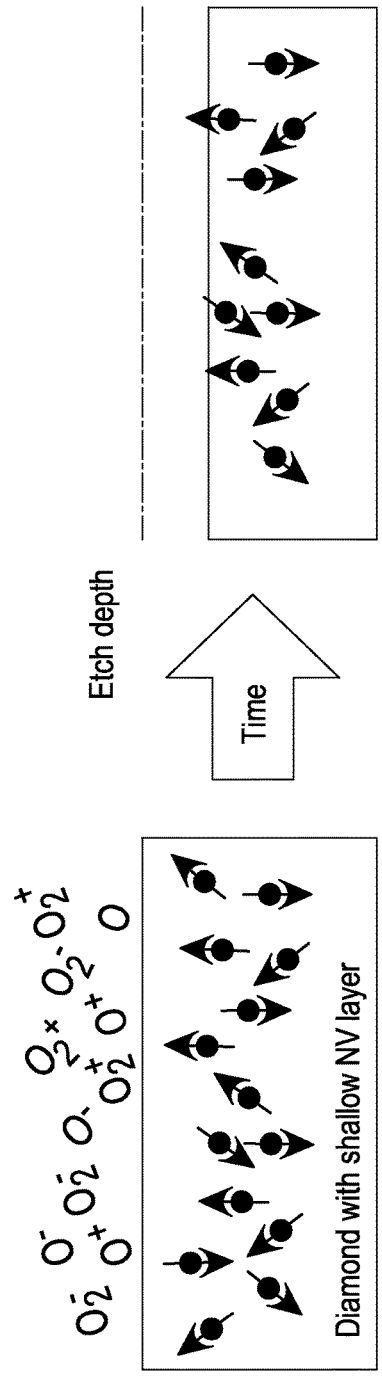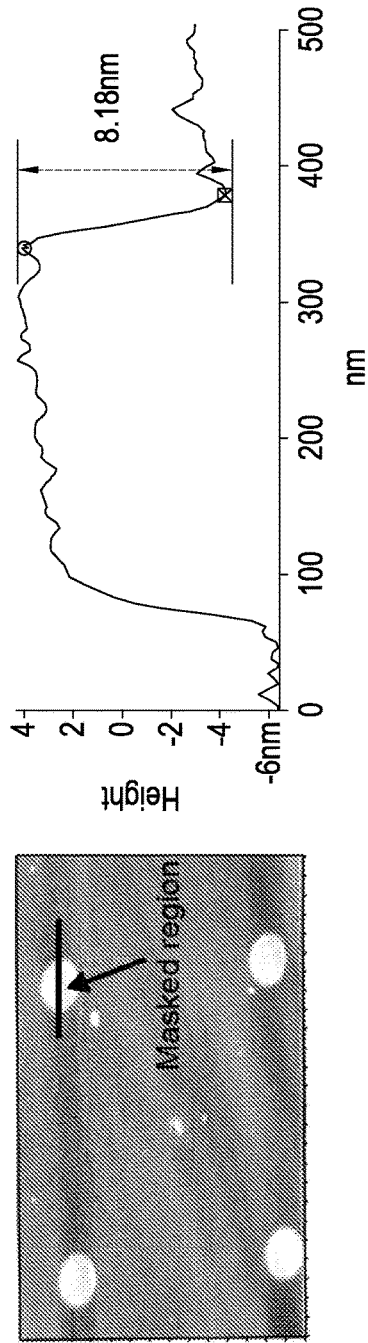
Fig. 13A

NANOSCALE SCANNING SENSORS

CROSS-REFERENCE TO RELATED APPLICATIONS

This application is a 35 U.S.C. § 371 National Phase Entry Application of International Application No. PCT/US2013/055644, filed Aug. 20, 2013, which designates the U.S., and claims the benefit of priority under 35 U.S.C. 119(c) from U.S. Provisional Patent Application Ser. No. 61/692,077 (the "'077 provisional application"), filed Aug. 22, 2012, entitled "Nanoscale Scanning Sensors." The contents of each of these applications are incorporated herein by reference in their entireties as though fully set forth.

STATEMENT REGARDING FEDERALLY SPONSORED RESEARCH

This invention was made with government support under contract number 60NANB10D002 awarded by the NIST; contract number HR0011-09-1-0005 by DARPA; and contract number HR0011-10-1-0073 by DARPA. The government has certain rights in the invention.

BACKGROUND

Spin defects in solid state systems, such as the NV (nitrogen-vacancy) defect centre in diamond, have numerous potential applications. These applications include, without limitation, nanoscale electric and magnetic-field sensing, single-photon microscopy, quantum information processing, and bioimaging.

NV-centre based nanosensors rely on the ability to position a single nitrogen-vacancy centre within a few nanometers of a sample, and then scan it across the sample surface, while preserving the NV centre's spin coherence and readout fidelity.

Existing scanning techniques, however, suffer from drawbacks that include low sensitivity, low resolution, and high data acquisition times. It is considered that these drawbacks are due to a number of factors including one or more of: short spin coherence times due to poor crystal quality; too large a distance between the spin defect and the sample surface being analyzed; variations in the distance between the spin defect and the sample surface being analyzed; and inefficient far-field collection of the fluorescence from the NV centre.

For example, one known technique utilizes a diamond nano-particle containing an NV spin defect. The diamond nanoparticle is adhered to an optical fiber to optically address the NV defect within the diamond nano-particle, a microwave generator is utilized to manipulate the spin state of the NV defect when the diamond nano-particle is placed in close proximity to a sample to be analyzed, and a detector is provided on an opposite side of the sample to detect fluorescence from the NV defect.

The aforementioned configuration has a number of problems. First, while the use of a diamond nano-particle ensures that the NV defect can be positioned close to the sample to be analyzed, diamond nano-particles tend to be of poor diamond quality and the NV defects therein have short spin coherence times and can be optically unstable leading to poor sensitivity. Secondly, fluorescent light is emitted in all directions and only a small proportion can be detected. Thirdly, the detector is disposed on an opposite side of the sample to the diamond nano-particle and thus the configuration can only be used for material samples which are transparent to the fluorescent emission. While the optical detector could be positioned on the same side of the sample as the diamond nano-particle, it is difficult to arrange the detector to effectively capture fluorescent emission because the diamond nano-particle is adhered to the end of an optical fiber which inhibits detection of fluorescence on the same side of the nano-particle as the optical fiber.

An alternative to the aforementioned configuration would be to use a high quality single crystal diamond material comprising an NV defect which has a longer spin coherence time. However, the use of a micron scale single crystal diamond material has a number of problems including, for example: too large a distance between the spin defect and the sample surface being analyzed; variations in the distance between the spin defect and the sample surface being analyzed; and inefficient far-field collection of the fluorescence from the NV centre.

It is an aim of certain embodiments of the present invention to solve one or more of the aforementioned problems.

SUMMARY OF INVENTION

According to one aspect of the present invention there is provided a system comprising: a sensing probe formed of a diamond material comprising one or more spin defects configured to emit fluorescent light, said one or more spin defects being located no more than 50 nm of a sensing surface of the sensing probe, the sensing probe further comprising an optical outcoupling structure formed by the diamond material, the optical outcoupling structure configured to optically guide the fluorescent light emitted by the one or more spin defects toward an output end of the optical outcoupling structure; an optical excitation source configured to generate excitation light directed to the one or more spin defects causing the one or more spin defects to fluoresce; an optical detector configured to detect the fluorescent light that is emitted from the one or more spin defect and that exits through the output end of the optical outcoupling structure after being optically guided therethrough; and a mounting system configured to hold the sensing probe so as to control a distance between the sensing surface of the sensing probe and a surface of a sample while permitting relative motion between the sensing surface of the sensing probe and the sample surface.

According to a second aspect of the present invention there is provided a sensing probe for use in the aforementioned system. The sensing probe is formed of a diamond material and comprises: one or more spin defects configured to emit fluorescent light; and an optical outcoupling structure formed by the diamond material, the optical outcoupling structure configured to optically guide the fluorescent light emitted by the one or more spin defects toward an output end of the optical outcoupling structure, wherein the one or more spin defects are located no more than 50 nm from a sensing surface of the sensing probe.

Certain further aspects of the present invention relate to sensing methods as described and claimed herein.

Certain embodiments of the present invention have improved sensitivity, higher resolution, and lower data acquisition times when compared with prior art arrangements. These advantageous features are achieved through the provision of a combination of: a small and controlled distance between spin defects and a sample surface being analyzed by locating one or more spin defects very close to a sensing surface of the diamond material while retaining the spin coherence properties of the spin defects; and efficient far-field collection of spin defect fluorescence through the provision of an optical outcoupling structure coupled to the one or more spin defects located close to the sensing surface.

The one or more spin defects may be located no more than 40 nm, 30 nm, 20 nm, 15 nm, 12 nm, or 10 nm from the sensing surface of the sensing probe. Typically the sensitivity of the system will be increased by locating the one or more spin defects closer to the sensing surface as a field to be sensed will decrease in intensity with increasing distance from a sample surface. By locating the one or more spin defects closer to the sensing surface of the sensing probe then the one or more spin defects can be positioned closer to a sample surface therefore increasing sensitivity. Furthermore, resolution can also be improved by enabling the one or more spin defects to be located closer to a sample surface.

Further improvements in sensitivity can be achieved through the provision of spin defects which have relatively long spin coherence times due to the use of good quality diamond material (preferably high quality single crystal diamond material). It is not straightforward to provide such long spin coherence defects close to a sensing surface as the spin coherence properties of spin defects are detrimentally affected by surface interactions and/or the processing steps required to process back a surface to reduce the surface-spin defect distance. As described in more detail later in this specification, the present inventors have developed processing techniques to fabricate optical outcoupling structures with one or more spin defects located therein close to a sensing surface while at the same time retaining the spin coherence properties of the spin defects. As such, the decoherence time of the one or more spin defects may be greater than 10 μsec, 50 μsec, 100 μsec, 200 μsec, 300 μsec, 500 μsec, or 700 μsec.

In order to provide a system which has high resolution, it is advantageous to provide relatively few, and ideally one, spin defect located close to the sensing surface and coupled to the optical outcoupling structure. For example, the sensing probe may comprise no more than 50, 30, 10, 5, 3, 2, or 1 spin defects located close to the sensing surface and optically coupled to the optical outcoupling structure (e.g. by locating the spin defects within the optical outcoupling structure near a sensing surface thereof). In the case that only one near surface spin defect (or relatively few) are provided to improve resolution, it is advantageous that such a spin defect has a long decoherence time as previously described to improve sensitivity.

Alternatively to the above, if very high resolution is not a requirement for certain applications then a larger number of spin defects may be provided. For example, the sensing probe may comprise a plurality of spin defects (e.g. more than 50) in the form of a layer located no more than 50 nm from the sensing surface and optically coupled to the optical outcoupling structure. In this case, each individual spin defect is not required to have such a high decoherence time to achieve good sensitivity due to the large number of individual spin defects acting as sensing elements. As such, sensitivity can be retained but at the expense of lower resolution.

In certain embodiments the sensing probe including the optical outcoupling structure is formed of a diamond component having at least one linear dimension greater than 1 μm in length. For example, the sensing probe including the optical outcoupling structure may be formed of a micron scale (or even millimeter scale) single crystal diamond material. Such a sensing probe has three advantageous over diamond nano-particles: (i) an optical outcoupling structure can more readily be fabricated into a larger piece of diamond material; (ii) a detector can be more readily located relative to the one or more spin defects and other components of the system such as the optical excitation source and mounting system whereby detection can be achieved with efficiency on the same side of a sample as the sensing probe; (iii) using larger scale, high quality diamond material enables the fabrication of better quality spin defects in terms of coherence time and spectral stability.

A number of possible optical outcoupling structure could be fabricated into the diamond material of the sensing probe including a nanopillar or a solid immersion lens. Optical outcoupling can also be effected via internal reflection, i.e. using the macroscopic shape of the diamond sensing probe to reflect light towards an output surface where the optical detector is located. It is considered that the use of a nanopillar as the outcoupling structure is a preferable option with one or more spin defects located at a distal end of the nano pillar, the proximal end of the nanopillar being attached to a micron scale diamond support. As described in more detail later, processing methodology has been developed to fabricate a nanopillar into a high quality single crystal diamond support with a good quality spin defect located very close to the distal end of the nanopillar. The nanopillar can be processed to have dimensions suitable for waveguiding fluorescent emission from the spin defect(s) located therein as well as optimizing the number of spin defects present within the nanopillar to achieve good resolution. For example, the nanopillar may have a diameter between 100 nm and 300 nm, and a length between 0.5 μm and 5 μm. Furthermore, the nanopillar can be principally aligned along a crystallographic axis, the crystallographic axis comprising one of: a <111> axis; a <110> axis; and a <100> axis. By the provision of an optical outcoupling structure as described herein it is possible to achieve an optical collection efficiency for the emitted fluorescent light between 0.01 to 0.10. Furthermore, it is possible to achieve a fluorescent photon count rate of greater than 50,000 counts/s, 100,000 counts/s, 150,000 counts/s, 200,000 counts/s, 250,000 counts/s, or 300,000 counts/s The mounting system is advantageously configured to position the one or more spin defects within a few nanometers of a sample and scan across a sample surface. For example, the mounting system may comprise an AFM (atomic force microscope). An optical microscope can be coupled to the mounting system and configured to optically address and readout the one or more spin defects. For example, the optical microscope may be a confocal microscope that is integrated with an AFM.

The system may further comprise a further source of electromagnetic radiation to manipulate the spin state of the one or more spin defects. For example, a microwave source, may be configured to generate microwaves tuned to a resonant frequency of the one or more spin defects. When the one or more spin defects are NV defects, the system can be configured to detect an external magnetic field by measuring a Zeeman shift of spin states in the NV defects via microwave manipulation of the spin defects in combination with fluorescence detection. To further improve spin coherence, and thus sensitivity, the microwaves may comprise a spin-decoupling sequence of pulses, wherein the sequence includes at least one of: a Hahn spin-echo pulse sequence; a CPMG (Can Purcell Meiboom Gill) pulse sequence; an XY pulse sequence; and a MREVB pulse sequence.

Utilizing the aforementioned methodology it is possible to configure the system to have an AC magnetic field detection sensitivity better than 200, 100, 75, 60, 50, 25, 10, or 5 nT Hz$^{-1/2}$ (e.g. at frequencies between 33 kHz and 10 MHz) and a DC magnetic field detection sensitivity better than 50, 20, 10, 6, 4, 1, or 0.5 $\mu T\ Hz^{-1/2}$. Furthermore, it is possible to configure the system to resolve single spin defects in a sample. Further still, due to the improvements described herein it is possible to significantly reduce the required integration time for single spin imaging while simultaneously achieving a good high signal to noise ratio, e.g. a signal to noise ratio of at least 2 with an integration time of no more than 10 mins (minutes), 5 mins, 3 mins, 2 mins, 1 min, 30 seconds, 15 seconds, 10 seconds, 5 seconds, 2 seconds, 1 second, or 0.5 second.

While high sensitivity magnetometry can be achieved as indicated above, electric field sensing and temperature sensing are also envisaged. For example, where the one or more spin defects are NV defects, the system can be configured to detect an external electric field by measuring a Stark shift caused by the external electric field mixing $m_s=+1$ and $m_s=-1$ states in the NV defects. Alternatively, or additionally, the system can be configured to detect a temperature using the NV defects, by measuring variation of axial zero-field splitting (ZFS) parameter of the NV centres. Temperature detection can also be used to calibrate out the effects of temperature on magnetic field sensing. For example, the system can be configured to monitor a temperature of the diamond material of the sensing probe so that one or more temperature-dependent effects on the detection of the magnetic field can be calibrated out. Alternatively, both $m_s=+1$ and $m_s=-1$ resonances can be measured so as to provide a feedback mechanism for calibrating out the one or more temperature-dependent effects. As such, the system can be configured to provide magnetic field measurements that are unaffected by temperature by using the $m_s=\pm 1$ resonance transitions.

Embodiments of the present invention also provide methods of using systems such as described herein. Such methods comprise: movably positioning an optical outcoupling structure of a sensing probe with respect to a surface of a sample; wherein the optical outcoupling structure contains one or more spin defects, and is configured to optically guide fluorescent light emitted by the spin defects toward an output end of the optical outcoupling structure; irradiating the spin defects with excitation light and microwaves so as to cause the spin defects to emit fluorescent light; and detecting the emitted fluorescent light that exits through the output end of the optical outcoupling structure after the fluorescent light has been optically guided through the optical outcoupling structure. Such methods may further comprise scanning the sample surface while maintaining a desired distance between the spin defects and the sample surface, so as to obtain information about the sample surface. The provision of a movable optical outcoupling structure in combination with one or more spin defects which can be located in a controlled manner close to a sample enables sensing with high sensitivity, high resolution, and low data acquisition times.

In addition to the above, it has been found that the one or more spin defects can be reliably and accurately positioned close to a sensing surface by utilizing a method comprising: movably positioning an optical outcoupling structure of a sensing probe with respect to a sample; wherein the optical outcoupling structure contains a spin defect configured to emit fluorescent light in response to excitation light from an optical source and microwaves from a microwave source; and wherein the optical outcoupling structure is configured to optically guide fluorescent light emitted by the spin defect toward an output end of the optical outcoupling structure; measuring a distance between the spin defect and the sample; etching a distal end of the optical outcoupling structure so as to reduce the distance between the spin defect and the sample; and repeating the acts of measuring said distance and etching said distal end of said optical outcoupling structure, until the distance has been reduced by a desired amount.

Further still, it has been found that contamination of a sensing probe during use can lead to a reduction in performance. As such, a methodology has been developed to clean the sensing probe to retain high performance. Such a method comprises: providing a sensing probe formed of a diamond material comprising one or more spin defects configured to emit fluorescent light, the sensing probe further comprising a diamond nanopillar configured to optically guide the fluorescent light emitted by the spin defect toward an output end of the nanopillar; scanning, without AFM feedback, a sharp tip of a sample with the nanopillar, by moving the diamond nanopillar with respect to the sample tip; and repeating the act of scanning, without AFM feedback, the sharp tip of the sample with the nanopillar, until contamination of the nanopillar is reduced by a desired amount.

BRIEF DESCRIPTION OF THE DRAWINGS

The drawings disclose illustrative embodiments. They do not set forth all embodiments. Other embodiments may be used in addition or instead.

FIG. 7A shows the current distribution used to simulate magnetic bits that were imaged with an NV scanning sensor.

FIG. 7B shows the magnetic field, projected on the NV axis, generated by the current distribution in FIG. 7A.

FIG. 7C illustrates the NV magnetometry response obtained from the magnetic field distribution shown in FIG. 7B.

FIGS. 13A-13G illustrate back-etching that allows the NV distance to be further reduced.

DETAILED DESCRIPTION

Illustrative embodiments are discussed in this application. Other embodiments may be used in addition or instead.

It should be understood that the present application is not limited to the particular embodiments described, as such may vary. Also, the terminology used herein is for the purpose of describing particular embodiments only, and is not intended to be limiting, since the scope of the present application will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of concepts described in the present application, a limited number of the exemplary methods and materials are described herein.

Where a range of values is provided, each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

In the present disclosure, methods and systems are described relating to nanoscale scanning sensors that are based on spin defects, for example NV centres. In some embodiments, the nanoscale scanning probes implement topside collection in conjunction with combined AFM and optical microscope.

Nanoscale sensing based on spin defects such as NV$^-$ centres is possible because the NV$^-$ centre forms a bright and stable single-photon source for optical imaging and has a spin-triplet ground state that offers excellent temperature, magnetic and electric field sensing capabilities, as described in further detail below. Note that in the rest of this document the negative charge state of the NV defect will be denoted simply as NV. Factors that contribute to the excellent performance of the NV centre in such spin-based sensing schemes include, without limitation, long NV spin coherence times, and efficient optical spin preparation and readout. These properties persist from cryogenic temperatures to ambient conditions, a feature that distinguishes the NV centre from other systems that have been proposed as quantum sensors, such as single molecules or quantum dots.

Figure 1A:
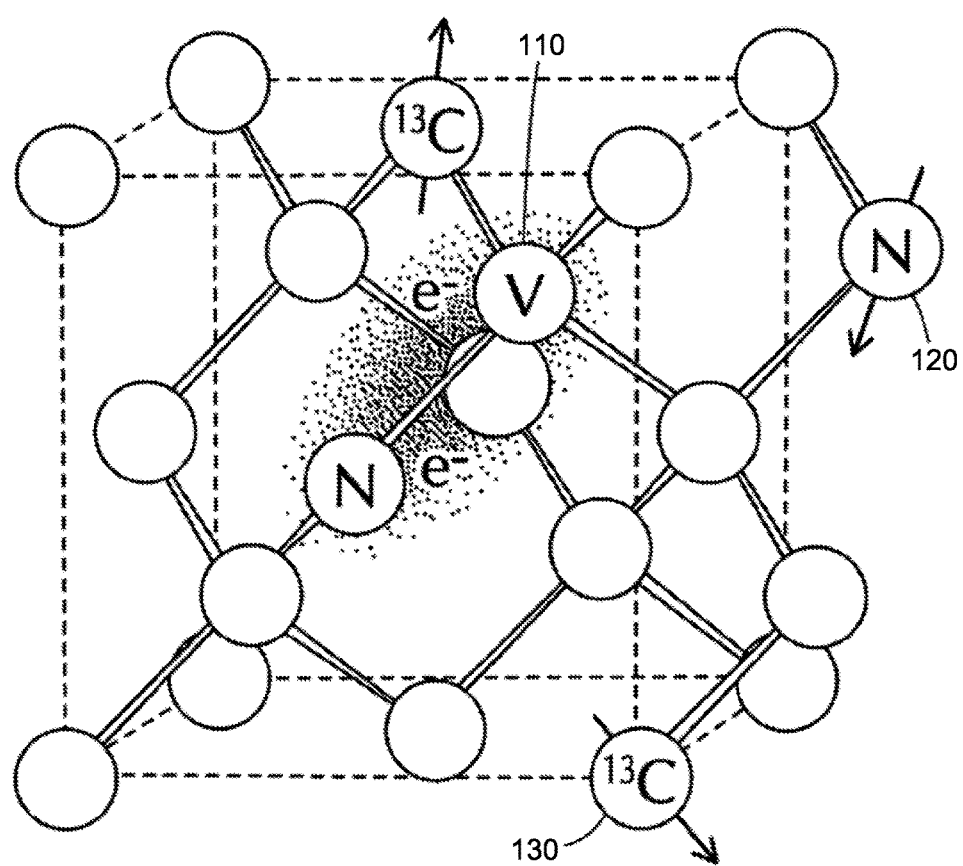
FIG. 1A illustrates an NV centre consisting of a substitutional nitrogen atom neighboring a lattice vacancy.

FIG. 1A illustrates an NV centre consisting of a substitutional nitrogen atom 120 neighboring a lattice vacancy 110. As seen in FIG. 1A, the NV centre is an empty position or vacancy 110, resulting from a missing carbon atom 130 in the diamond lattice. An NV centre is relatively insulated from magnetic interference from other spins. The quantum state of the spin of the NV centre may be probed and controlled at room temperature. NV centres in diamond, as well as systems involving other types of defects in solid state lattices, can provide electronic spins that have very little interaction with the background lattice. Such electronic spins are optically detectable with unique optical signatures. NV centres are visible as red spots when illuminated by laser.

Figure 1B:
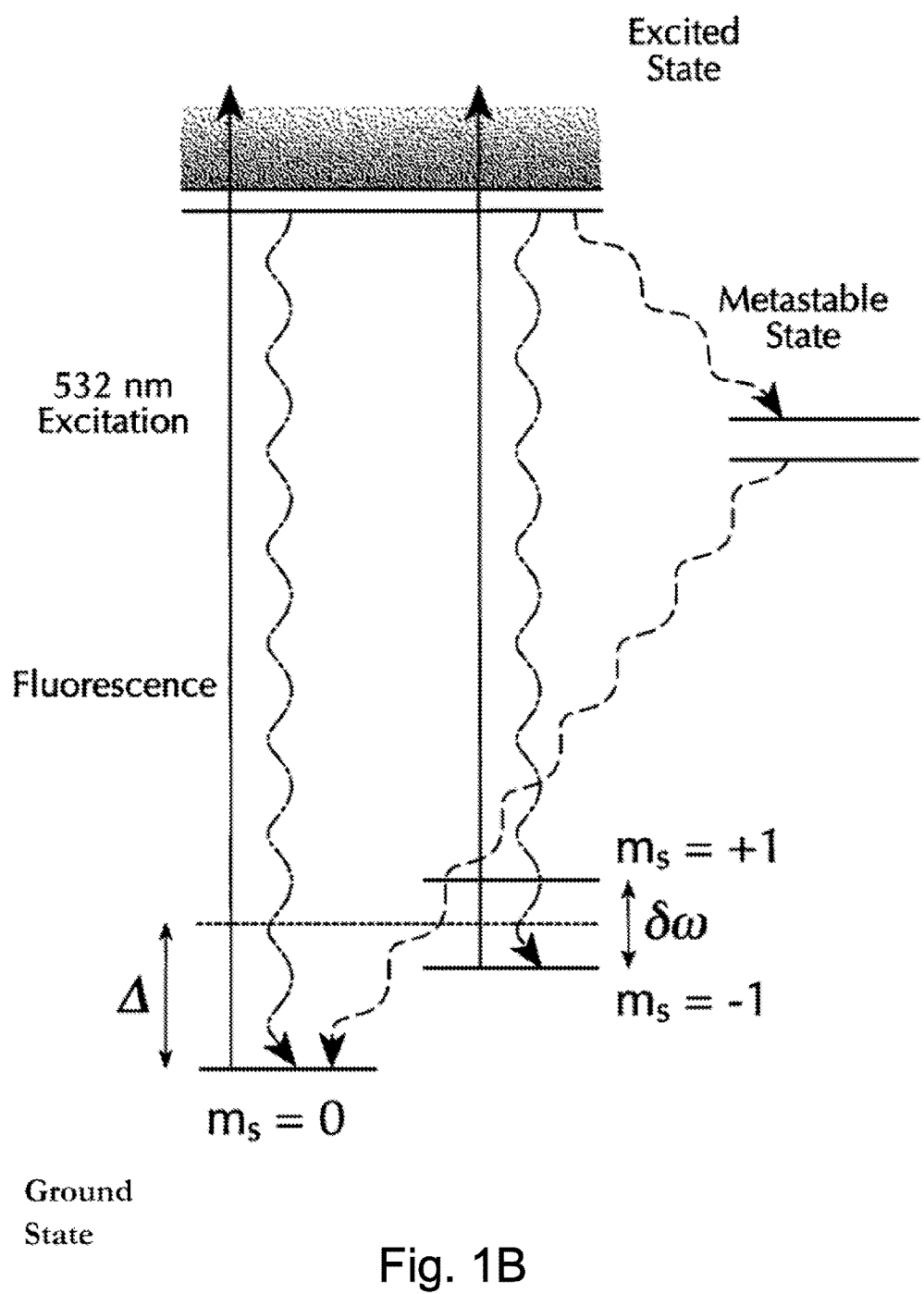
FIG. 1B shows the electronic structure of an NV centre in diamond.

FIG. 1B shows the electronic structure of an NV centre in diamond. As seen in FIG. 1B, the NV centre's ground state is paramagnetic and a spin one (S=1) triplet. The ground state of the NV centre is split into $m_s$=0 and doubly degenerate $m_s$=±1 sublevels, with a Δ=2.87 GHz crystal field splitting. The NV centre emits fluorescent radiation from its transitions between the electronic ground and excited states. The electronic transition is spin preserving, and the $m_s$=0 transition is brighter than the $m_s$=±1 transition. Microwave excitation at the resonance frequency causes a fluorescence drop, allowing the resonance frequency to be measured by fluorescence measurement.

A static external field causes a Zeeman shift between $m_s$=+1 and $m_s$=−1 states, which is determined by a gyromagnetic ratio γ=2.8 MHz/G. The degeneracy of the $m_s$=±1 states is thus lifted, under the external field, and the electron paramagnetic resonance spectrum contains two resonance lines, one shifted to the higher and the other shifted to the lower frequency. By measuring the two shifted resonance frequencies and their difference δω, the magnitude of the external field can be calculated.

As well as being able to detect magnetic fields using the NV defect it has also been shown that it can be used to measure temperature (Phys. Rev. X 2, 031001 (2012)) and electric fields (Nature Physics Volume 7, Pages 459-463 (2011)). This could have a wide range of uses when combined with certain embodiments of the present invention. For example detection of the electric field, magnetic field and temperature in a biological specimen.

It is know in the art that the axial zero-field splitting (ZFS) parameter, D (2.87 GHz), varies significantly with temperature which provides a technical challenge for room-temperature diamond magnetometry as described in (Phys. Rev. B 82, 201202(R) (2010)). This property can be used in order to deduce temperature i.e. in this invention a nanoscale temperature sensor. For accurate B-field sensing it may be desirable circumvent this temperature effect. Such methods might include: 1) a temperature sensor to monitor the temperature of the diamond which the allows the effect of temperature to be calibrated out; 2) Measurement of both the $m_s=\pm 1$ resonances to provide a feedback mechanism for controlling this; and 3) Use of the $m_s=\pm 1$ resonances transitions to provide the magnetic field measurement (opposed to the transition between the $m_s=0$ and $m_s=\pm 1$) which are unaffected by temperature.

These methods to negate the effects of temperature variances during measurement combined with certain embodiments of the present invention allow for an improved sensing device.

An electric field at the NV centre can mix the $m_s=+1$ and $m_s=-1$ states, causing a shift in its ZFS. Under the presence of small magnetic fields (compared to the NV centre's strain), this shift comprises a (linear) Stark shift, which can be measured with high sensitivity. For this particular embodiment, AC electric field sensitivities ranging from 50 to 200 $Vcm^{-1} Hz^{-1/2}$ are achievable. For sensitivities in this range (e.g. 120 $Vcm^{-1} Hz^{-1/2}$), within 1 second of integration time, a field equivalent to 0.01 electron charges at a distance of 10 nm could be detected (signal to noise of 1).

Variations in temperature at the NV centre induce changes in the lattice constant which modify the local crystal field at the NV centre and shift the ZFS. Thus, by measuring the ZFS the NV centre additionally can operate as a sensitive thermometer. For this specified embodiment, the temperature can be measured with a sensitivity ranging from 0.2 to 0.8 $KHz^{-1/2}$.

Due to the above-described optical and magnetic properties of NV centres, NV centres can be used as sensor probes. In order for an NV centre to be a useful probe, the NV centre must be positioned with nanometer accuracy, while simultaneously its fluorescence is being measured. This can be achieved by using NV centres as sensor probes in conjunction with AFM methods combined with optical microscopy.

While some success has been achieved at implementing scanning NV sensors using diamond nanocrystals grafted onto scanning AFM probe tips, these approaches suffer from the poor sensing performance of nanocrystal-based NV centres, for which the spin coherence times are typically orders of magnitude shorter than for NV centres in bulk diamond.

In the present application, NV sensors are disclosed that use a diamond nanopillar as the scanning probe of an AFM, with an individual NV within a few nanometers of its distal end.

The NV might be placed through one or some combination of implantation, as grown, formed through irradiation and annealing.

Figure 2:
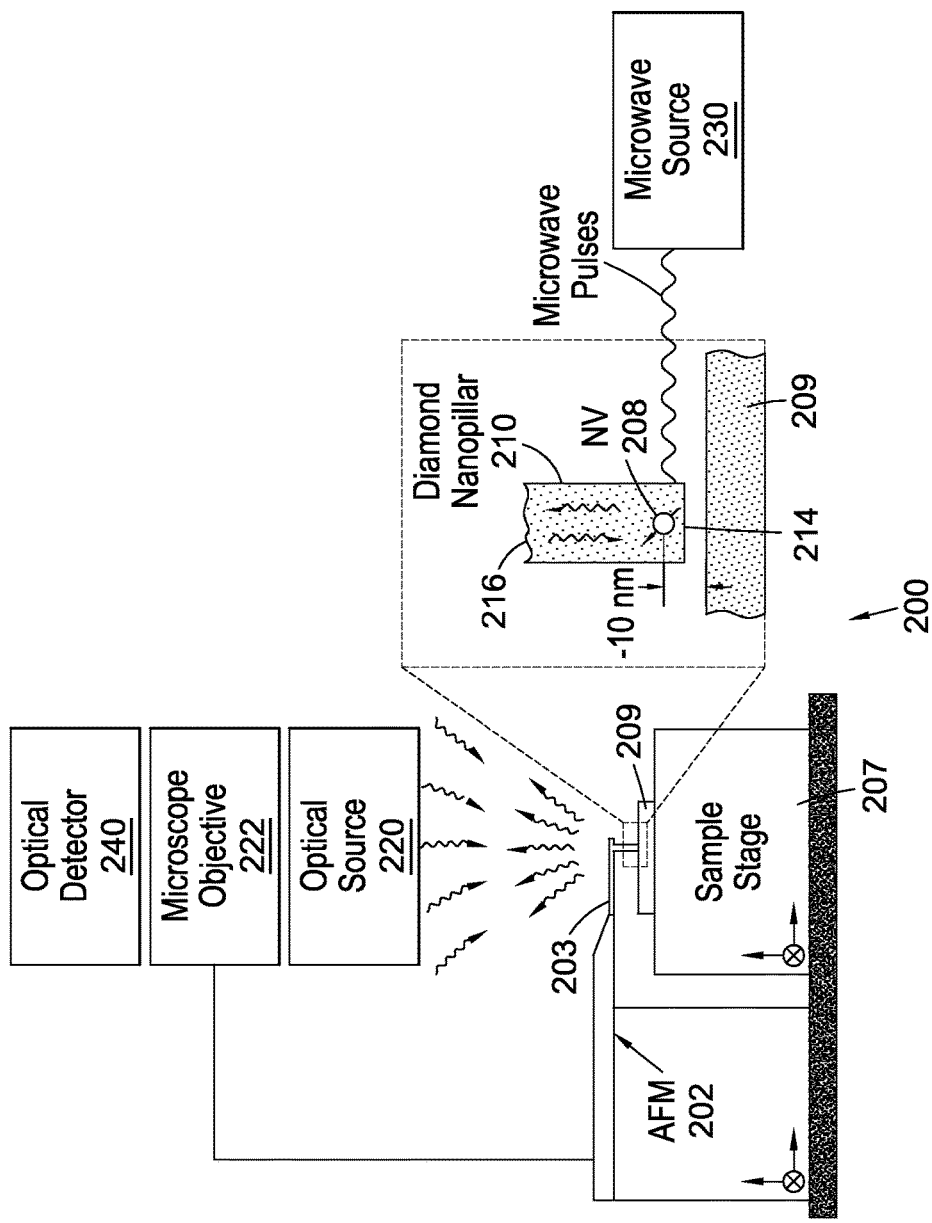
FIG. 2 is a schematic block diagram of a nanoscale scanning NV sensor system that implements topside collection, in accordance with one or more embodiments of the present application.

FIG. 2 is a schematic block diagram of a nanoscale scanning NV sensor system 200 that allows for topside collection, in accordance with one or more embodiments of the present application. The system 200 includes a monolithic scanning NV sensor that uses a diamond nanopillar 210 as the scanning probe, with an individual NV centre 208 artificially created at a small distance, for example about 25 nm, from a distal end of the diamond nanopillar.

The system 200 includes a combined AFM 202 and optical microscope, i.e. an AFM 202 that is used together with the optical microscope. In some embodiments, the AFM 202 and the optical microscope may be integrated into a single instrument. In the illustrated embodiment, the optical microscope is a confocal microscope including a confocal microscope objective 222.

The AFM 202 includes a diamond nanopillar 210 attached to a diamond cantilever 203 of the AFM 202. The diamond cantilever 203 may be attached to a positioning system 207, which for example may include a moveable stage on which a sample 209 can be placed, as shown in FIG. 2. The diamond nanopillar 210 is thus movably positioned relative to a surface of the sample 209, so that the sample surface can be scanned by the diamond nanopillar 210 using AFM feedback. In some embodiments, the positioning system 207 may include 3-axis piezoelectric positioners configured to position the sample and the AFM head with respect to a fixed optical axis of the optical microscope.

In some embodiments, micro-meter thin, single-crystalline diamond slabs 215 are fabricated to produce the diamond nanopillar 210. As described in further detail in conjunction with FIG. 4A below, the diamond nanopillar 210 can be fabricated so as to contain a single NV centre 208, which can be brought within a few tens of nanometers of target samples 209.

The diamond nanopillar 210 has an elongated configuration and includes a distal end 214 that can be positioned directly opposite a sample surface, and a proximal end 216 to be coupled to the AFM cantilever 203. The diamond nanopillar 210 is thus configured to optically guide the fluorescence emitted by the NV centre 208, in a direction generally extending from the distal end 214 toward the proximal end 216.

In the illustrated embodiment, the size of the diamond nanopillar 210 is about 200 nm in diameter, which optimizes the above-described optical waveguiding by the diamond nanopillar. Other embodiments may use different sizes for the diamond nanopillar 210, for example nanopillars that are less than 200 nm in diameter. In the illustrated embodiment, the size of the diamond cantilever 203 may be about 4 μm×30 μm in lateral dimensions, and about 2 μm in height. Other embodiments may use different sizes for the diamond cantilever, for example diamond cantilevers that have larger, or smaller, lateral dimensions and/or height.

The system 200 further includes an optical source 220 configured to generate excitation light that causes emission of fluorescent light from the color centres when applied thereto. In the illustrated embodiment, the optical source 220 is a 532-nm excitation laser. In other embodiments, different types of optical sources can be used. For example, the optical source may be a laser or an LED tunable to a wavelength less than 637 nm.

The microwave source 230 is configured to generate pulses of microwave radiation and to apply the microwave pulses to the NV centre 208. In some embodiments, the microwave source 230 is configured to apply to the NV centre microwave pulses tuned at the resonance frequency of the NV centre 208, during excitation of the NV centre by the laser light from the laser 220, and during scanning of the sample surface by the diamond nanopillar 210.

The microwave source may be configured to apply to the NV centre microwave pulses that allow for precession of the electronic spin of the NV centre about an external magnetic field to be sensed, the frequency of the precession being linearly related to the magnetic field by the Zeeman shift of the energy levels of the electronic spin, so that a strength of the external magnetic field can be determined from the measured Zeeman shift.

The microwave source may be configured to apply to the NV centre microwave pulses so that a strength of the external electric field can be determined from a measured shift in the energy levels of the electronic spin of the NV centre.

In some embodiments of the present application, topside collection is implemented. In these embodiments, the optical fluorescence from the NV centre 208 is read out from the topside of the cantilever 203 and thus through the entire nanopillar 210. In other words, the fluorescence emitted by the NV centre 208 is detected by the optical detector 240 after the fluorescent light from the NV centre 208 has been optically guided throughout the length of the diamond nanopillar 210 and exits through the proximal end 216 of the diamond nanopillar 210.

Topside readout allows for significantly improved performance of the NV sensor system 100. For example, topside readout allows the study of samples that are non-transparent to the fluorescence radiation from the NV centre 208. If bottom-side readout were used, as has been conventionally done, then the fluorescence would be collected through the sample itself, which severely limits the type of samples which can be studied.

Moreover, topside readout takes advantage of optical waveguiding from the diamond nanopillar 210 to enhance photon collection efficiency. In some embodiments, the collection efficiency may be improved by a factor of about 5. Such increased collection efficiency leads to an increased sensitivity, which is an important advantage in many applications.

By implementing the above-described topside collection using diamond nanopillars as described above, the excitation light, typically green laser at 532 nm, is better isolated from the samples. This can be important for imaging samples which react negatively to intense laser fields, for example biological samples. The amount of required power is minimized to saturate the NV fluorescence due to the above-described optical waveguiding by the diamond nanopillar 210. In some embodiments, there is a reduction of a factor of about 10 in saturation power. In addition, as the excitation light from the laser is focused on the waveguiding mode of the nanopillar, far-field excitation of the sample can be minimized.

In these embodiments, the system 200 includes at least one optical detector 240 that is positioned so as to receive the emitted fluorescent light that exits through the proximal end 216 of the diamond nanopillar 210, after being optically guided through the length of the diamond nanopillar as described above. Because diamond nanopillars are efficient waveguides for the NV fluorescence band, very high NV signal collection efficiencies can be achieved using the above-described topside collection method.

In these embodiments, the microscope objective 222 is disposed between the optical detector 240 and the topside of the cantilever 203, as seen in FIG. 2. The objective 222 may be a long-working-distance microscope objective 222. In some embodiments, the objective 222 may have a numerical aperture of about 0.7. Other embodiments may use microscope objectives with numerical apertures that are greater or less than 0.7.

The system 200 may also include one or more dichroic mirrors that separate the fluorescence emitted by the NV centre 208 from the excitation light generated by the laser 220.

The AFM 202 may include an AFM feedback system configured to control the distance between the NV centre and the sample surface. The spatial resolution of an NV sensor is affected by the distance from the NV centre to the sample. Proper AFM control, including without limitation mechanical control and feedback control, must be achieved to assure close proximity of the NV centre to the sample surface. Bad mounting and/or improper AFM feedback control can lead to excessive AFM tip-sample distances. In some embodiments, an AFM feedback system, for example provided by an Attocube ASC500 controller, may be used to proper setup and tuning of AFM feedback, which in conjunction with accurate mounting of AFM tips allows for precise observation of desired variables.

A processing system may be integrated with the system described above, and is configured to implement the methods, systems, and algorithms described in the present application. The processing system may include, or may consist of, any type of microprocessor, nanoprocessor, microchip, or nanochip. The processing system may be selectively configured and/or activated by a computer program stored therein. It may include a computer-usable medium in which such a computer program may be stored, to implement the methods and systems described above. The computer-usable medium may have stored therein computer-usable instructions for the processing system. The methods and systems in the present application have not been described with reference to any particular programming language; thus it will be appreciated that a variety of platforms and programming languages may be used to implement the teachings of the present application.

Figure 3A:
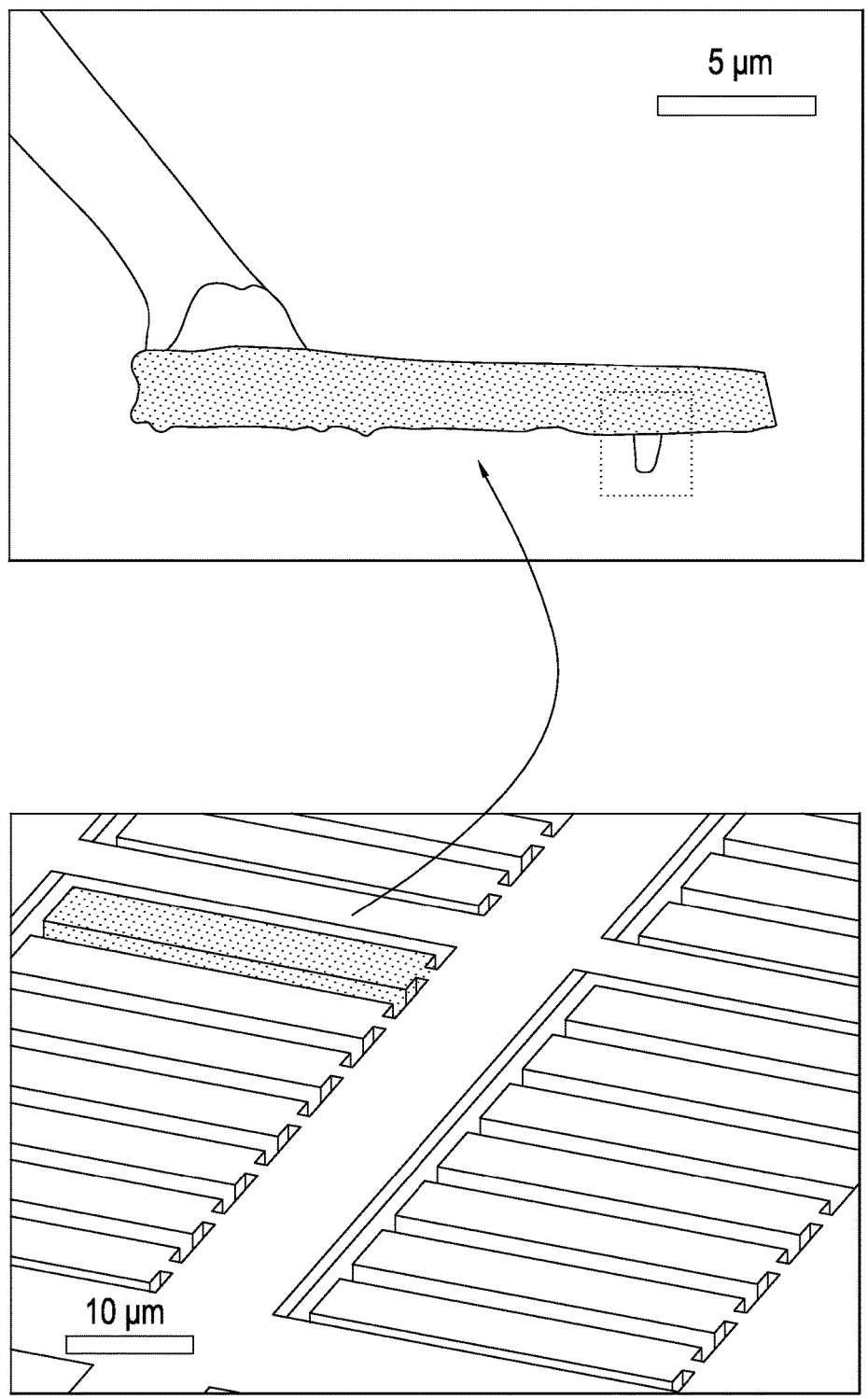
FIG. 3A shows a representative SEM (scanning electron microscope) image of a single-crystalline diamond scanning probe containing a single NV centre within ~25 nm of its tip, within an array of diamond platforms with nanopillars.

FIG. 3A shows a representative scanning electron microscope (SEM) image of a single-crystalline diamond scanning probe containing a single NV centre within ~25 nm of its tip. To prepare such devices; a series of fabrication steps are performed sequentially, including forming NV creation (e.g. through low-energy ion implantation), several successively aligned electron-beam lithography steps and reactive ion etching.

An important element to this sequence is the fabrication of micrometer-thin, single-crystalline diamond slabs that form the basis of the scanning probe device shown in FIG. 3A.

The scanning diamond nanopillars have typical diameters of ~200 nm and lengths of ~1 µm and are fabricated on few-micrometer-sized diamond platforms that are individually attached to atomic force microscope (AFM) tips for scanning.

Figure 3B:
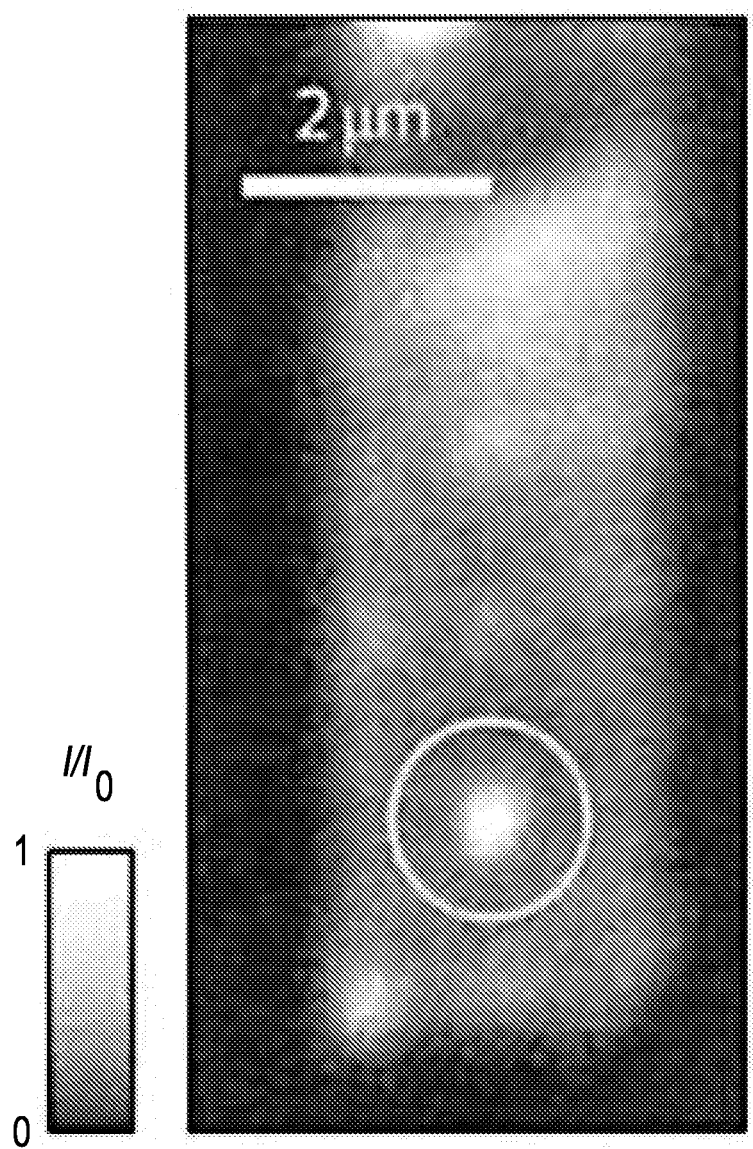
FIG. 3B is a confocal image of red fluorescence from a single-crystalline diamond probe.
Figure 3C:
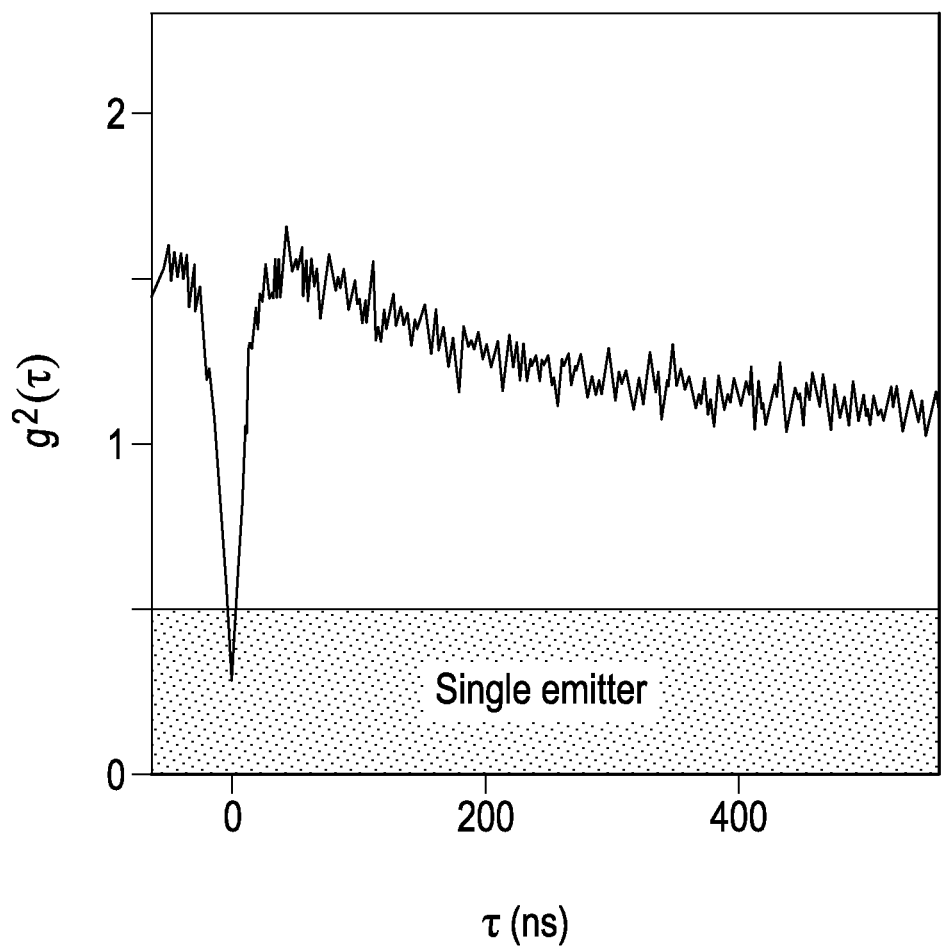
FIG. 3C illustrates photon autocorrelation measurement for NV fluorescence.

FIG. 3B shows a confocal image of red fluorescence from a single-crystalline diamond probe, whereas FIG. 3C illustrates photon autocorrelation measurement for the NV fluorescence. In FIG. 3B, a confocal scan was performed of a typical single scanning NV device, under green laser illumination, at an excitation wavelength of 532 nm. The bright photon emission emerging from the nanopillar (white circle) originate from a single NV centre, as indicated by the pronounced dip in the photon-autocorrelation measurement shown in FIG. 3B, and the characteristic signature of optically detected NV electron-spin resonance (ESR) seen in FIG. 3C. These results, all obtained from a same device, confirm that photon waveguiding through the nanopillar persists despite the close proximity of the NV to the tip of the fabricated nanopillar devices.

Figure 3D:
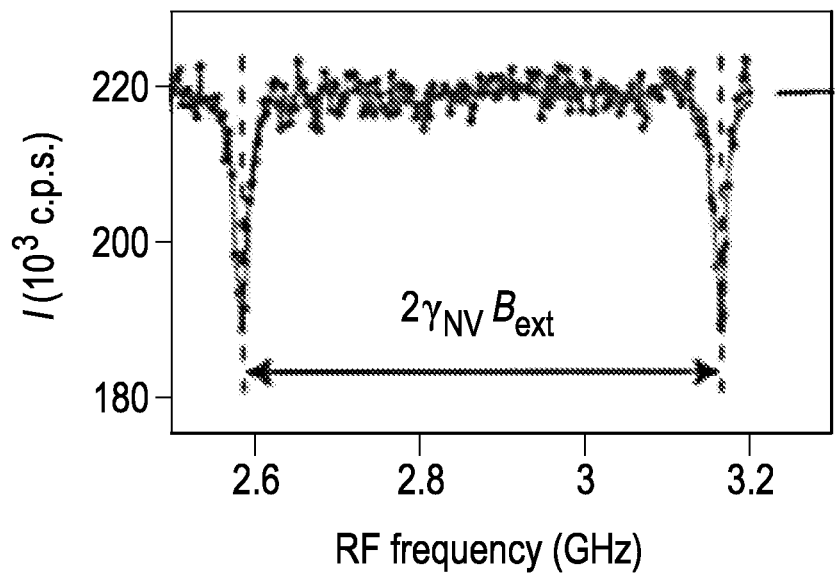
FIG. 3D illustrates optically detected ESR that identifies the single emitter in the nanopillar as an NV centre.

FIG. 3D illustrates optically detected ESR that identifies the single emitter in the nanopillar as an NV centre. The data in FIG. 3D were obtained at 100 µW excitation power and demonstrate single NV counts approaching $2.2 \times 10^5$ counts per second (c.p.s.)—an approximately fivefold increase in detected fluorescence intensity compared to an NV observed under similar conditions in an unpatterned diamond sample. Thus, there is a significant increase in fluorescence signal strength from the scanning NV and at the same time minimal exposure of the sample to green excitation light. This may be particularly relevant for possible biological or low-temperature applications of the scanning sensor.

Figure 3E:
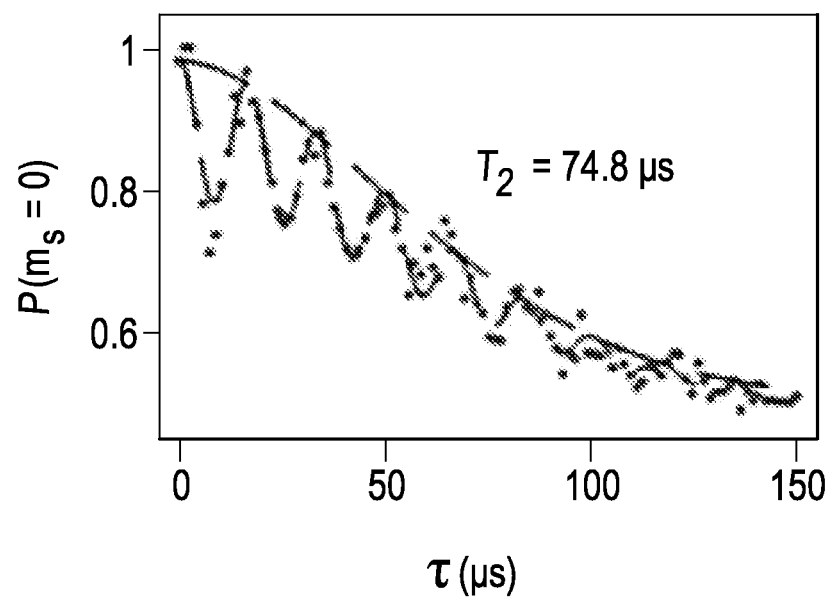
FIG. 3E illustrates spin-echo measurements for the NV centre in the diamond nanopillar device.

FIG. 3E illustrates spin-echo measurements for the NV centre in the diamond nanopillar device. The spin coherence time $T_2$ of the NV centre may be characterized using well-established techniques for coherent NV-spin manipulation. Spin-coherence sets the NV sensitivity to magnetic fields and limits the number of coherent operations that can be performed on an NV spin; it is therefore a figure of merit for applications in magnetic-field imaging and quantum information processing.

Using a Hahn-echo pulse sequence, the characteristic single NV coherence decay shown in FIG. 3E was measured. From the decay envelope a spin coherence time of $T_2=74.8$ µs was deduced. This $T_2$ time is consistent with the density of implanted nitrogen ions ($3 \times 10^{11}$ cm$^{-2}$) and it can be concluded that the device fabrication procedure fully preserves NV spin coherence. Combining measurements of the $T_2$ time with the fluorescence count rate and NV spin readout contrast as obtained above, a maximal a.c. magnetic field sensitivity of 56 nT Hz$^{-1/2}$ at a frequency of 33 kHz and, based on data in FIG. 3D, a d.c. sensitivity of 6.0 µT Hz$^{-1/2}$ was obtained.

Both a.c. and d.c. magnetic field sensitivities may be further improved by using spin-decoupling sequences and optimized parameters for spin readout, respectively. In some embodiments, ranges between about 10 nT Hz$^{-1/2}$ and 100 nT Hz$^{-1/2}$ may be attained for the a.c. magnetic field sensitivities. In some embodiments, a.c. sensitivities better than 200, 100, 75, 60, 50, 25, 10, or 5 nT Hz$^{-1/2}$ may be attained.

In some embodiments, ranges between about 0.5 µT Hz$^{-1/2}$ and 10 µT Hz$^{-1/2}$ may be attained for the d.c. magnetic field sensitivities. In some embodiments, d.c. sensitivities better than 50, 20, 10, 6, 4, 1, 0.5 µT Hz$^{-1/2}$ may be attained.

Figure 4A:
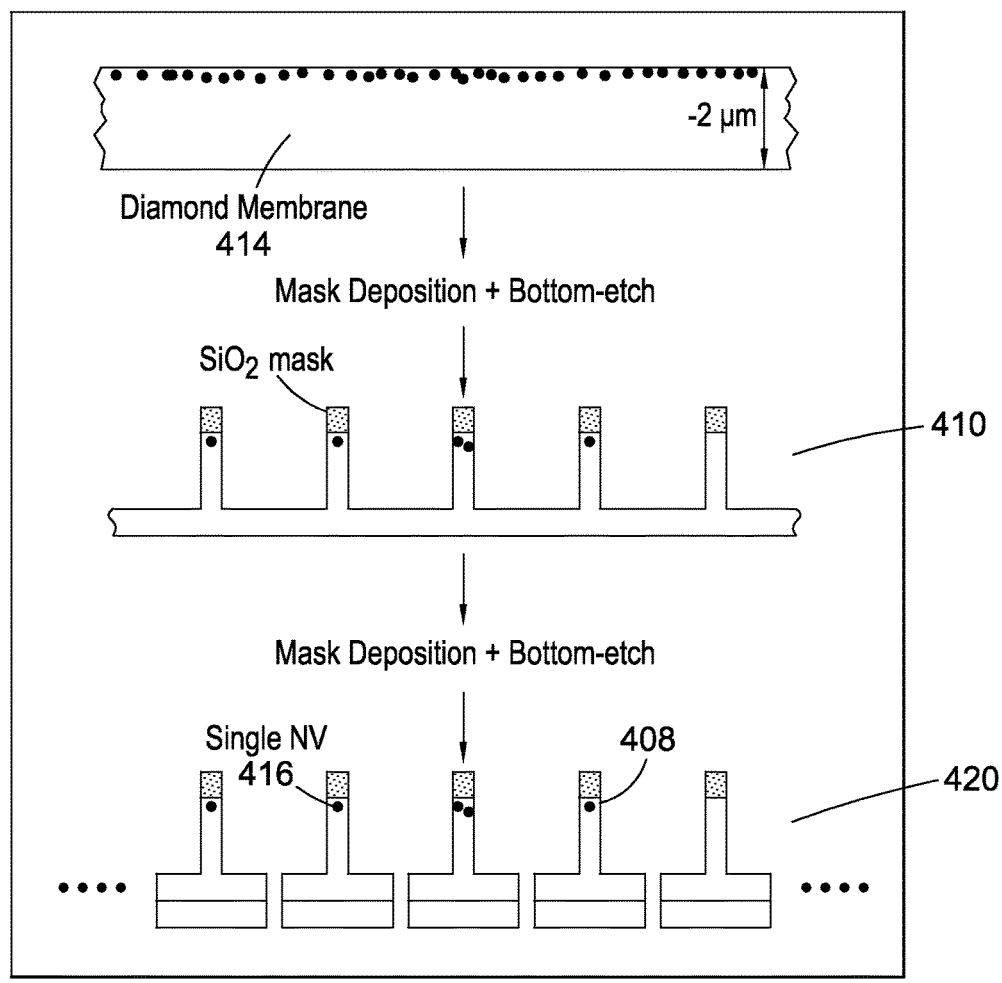
FIG. 4A schematically illustrates the fabrication of a diamond nanopillar, in accordance with one or more embodiments of the present disclosure.

FIG. 4A schematically illustrates the fabrication of a diamond nanopillar that is used as an AFM probe tip, in accordance with one or more embodiments of the present application. In overview, electron-beam lithography is used to define nanopillars and platforms from the top and bottom sides of the diamond membrane 414. Patterns are then transferred to the diamond by RIE (reactive ion etching). Mask deposition and top-etch results in an intermediate structure 410, which in the illustrated embodiment has a SiO$_2$ mask. Mask deposition and bottom-etch results in a structure 420, which allows creation of single NV centres 416 in each individual nanopillar 408 through ion implantation. The monolithic diamond membrane 414 may have a thickness on the order of a few micrometers.

In some embodiments, the structures described in the above paragraph may be fabricated from a sample of high-purity, single-crystalline diamond, which for example may be electronic grade diamond from Element Six. In the case of single crystal, the major face, i.e. that perpendicular to the eventual direction of the nano-pillar might be substantially (less than 10, 5, 2 degrees) from the principal crystallographic axes of {111}, {110} or {100}. In some cases polycrystalline or HPHT type diamond might also be suitable.

In one example the sample may be bombarded with atomic nitrogen at an energy of about 6 keV and a density of about $3 \times 10^{11}$ cm$^{-2}$, leading to a nominal mean NV depth of about 10 nm. Subsequent annealing at about 800 C for about 2 hours may yield a shallow layer of NV centres with a density of $\times 25$ NVs/µm$^2$ and a depth of about 25 nm.

In these embodiments, the sample is then etched from the non-implanted side to a thickness of about 3 µm using reactive ion etching. In some embodiments, a cyclic etching recipe may be used that includes a 10 min ArCl$_2$ etch, followed by 30 min of O$_2$ etching and a cooling step of 15 minutes. This sequence allowed the integrity of the diamond surface to be maintained during the few-hour etching time. On the resulting thin diamond membrane 414, an array of diamond nanopillars 210 can be fabricated on the top side by using electron-beam lithography and RIE as described above.

Figure 4B:
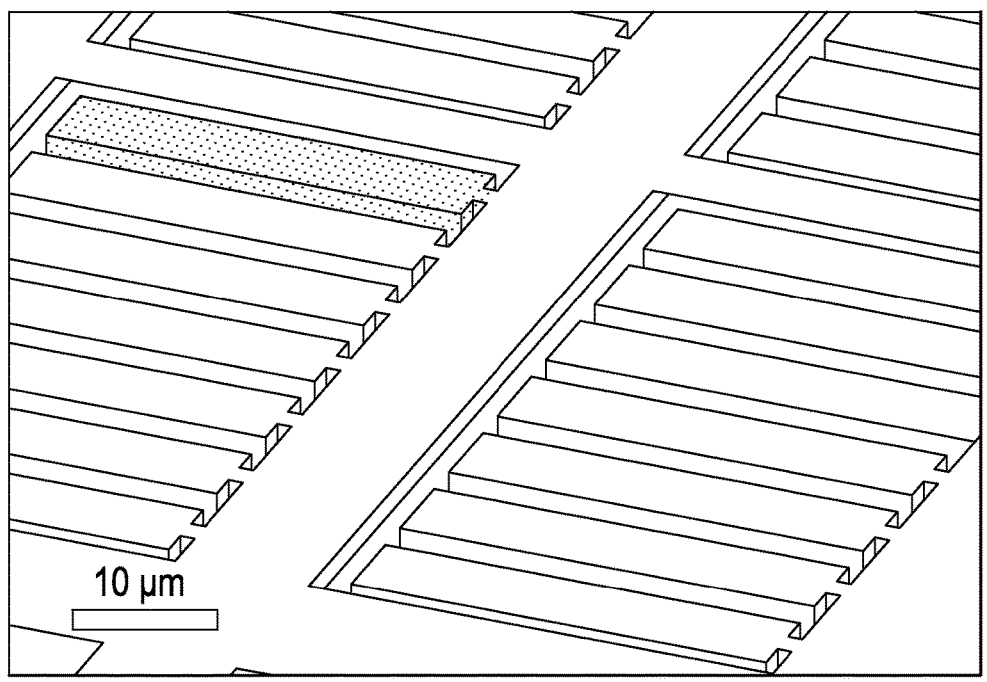
FIG. 4B shows an SEM image of the resulting array of diamond platforms with nanopillars.

Next, a second lithography step can be performed on the back-side of the diamond membrane, which defined platforms to hold the diamond nanopillars. A final RIE process transferred the resist pattern to the sample, and fully cut through the diamond membrane to yield the structure shown in FIG. 4A. FIG. 4B shows an SEM image of the resulting array of diamond platforms with nanopillars.

In a second example the NVs might be produced using growth alone, or through conversion of N to NV through using known methods in the art of irradiation (e.g. electron irradiation) and annealing.

In some embodiments, the nanoscale NV sensor systems described above can be applied to nanoscale magnetic sensing and/or imaging. For example, in one or more embodiments the system 100 may be used to sense the magnetic field generated by the spins contained in the sample 209 scanned by the diamond nanopillar 210. Standard spin-echo techniques may be used for coherent NV-spin manipulation. In these embodiments, the microwave source 230 is configured to apply to the NV centre microwave pulses that cause the spin of the NV centre to precess under the influence of a Zeeman shift, so that a strength of an external field can be determined from the measured Zeeman shift. For applications such as magnetic imaging, the microwave source 230 may be configured to apply the microwave pulses to the NV centre 208 while the diamond nanopillar 210 is scanning the sample surface, so that a magnetic field image of the sample surface can be obtained by the system 200.

Using well-established techniques for coherent NV-spin manipulation as mentioned above, the spin coherence time $T_2$ of the NV centre can be characterized. Spin-coherence sets the NV sensitivity to magnetic fields and limits the number of coherent operations that can be performed on an NV spin. Spin coherence is thus an essential figure of merit for applications in magnetic field imaging and quantum information processing.

To obtain information about single NV coherence decay, a Hahn-echo pulse sequence can be used. In this way, a spin coherence time of $T_2=74.9$ µs is obtained for the diamond nanopillar described in conjunction with FIG. 2 above. Examples of other decoupling pulse sequences that can be generated by the microwave source 230 include without limitation: a CPMG (Can Purcell Meiboom Gill) pulse sequence; an XY pulse sequence; and a MREVB pulse sequence.

Combining measurements of the $T_2$ time with measured values of the fluorescence count rate and NV spin readout contrast, an AC magnetic field sensitivity of about 56 nT $Hz^{-1/2}$ at a frequency of about 33 kHz, and a DC magnetic field sensitivity of about 6.0 µT $Hz^{-1/2}$ can be obtained for the embodiments described above. Both AC and DC magnetic field sensitivities can be further improved by using spin-decoupling sequences and/or optimized parameters for spin readout.

FIGS. 5A-5E illustrate methods and results relating to the imaging of a nanoscale magnetic memory medium characterize the resolving power of the scanning NV sensor. A nanoscale magnetic memory medium, consisting of bit tracks of alternating (out-of-plane) magnetization with various bit sizes, was imaged. The scanning NV sensor operated in a mode that imaged contours of constant magnetic field strength ($B_{NV}$) along the NV axis through the continuous monitoring of red NV fluorescence, in the presence of an ESR driving field of fixed frequency $\omega_{MW}$ and typical magnitude $B_{MW} \approx 2$ G, as determined from NV Rabi oscillations (not shown). $\omega_{MW}$ was detuned by $\delta_{MW}$ from the bare NV spin transition frequency $\omega_{MW}$, but local magnetic fields due to the sample changed this detuning during image acquisition. In particular, when local fields brought the spin transition of the NV into resonance with $\omega_{MW}$, a drop in NV fluorescence rate was observed, which in the image yielded a contour of constant of $B_{NV}\delta_{MW}/\gamma_{NV}$, with $\gamma_{NV}$=2.8 MHz $G^{-1}$ being the NV gyromagnetic ratio.

Figures 5A, 5B:
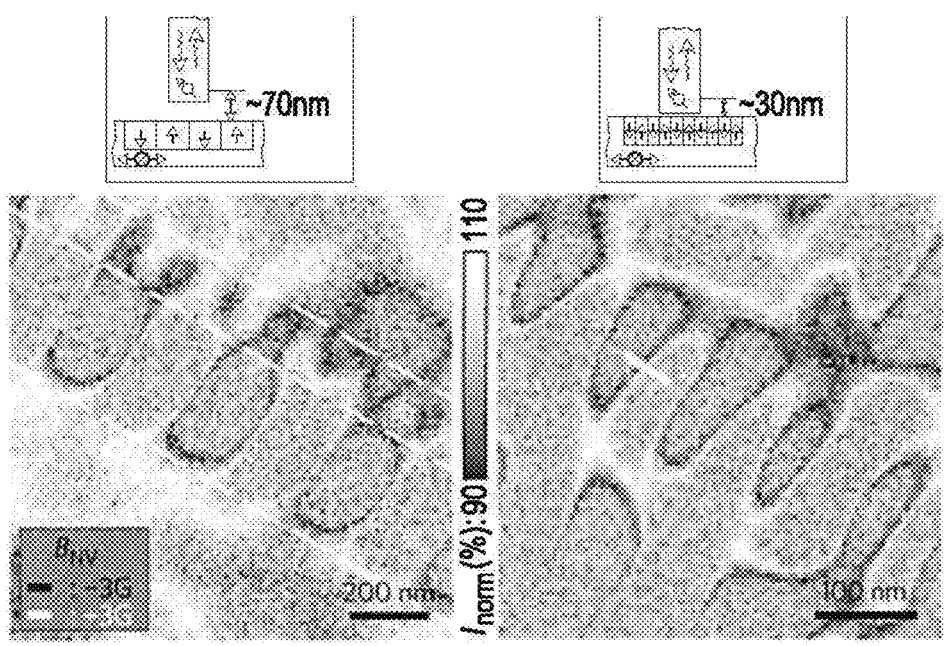
FIG. 5A shows an NV magnetic-field image of bit tracks on a magnetic memory.
FIG. 5B shows a similar magnetic image as in FIG. 5A, but with the NV-sample distance decreased by an estimated 50 nm.

FIG. 5A shows a resulting scanning NV magnetometry image of two stripes of magnetic bits, indicated by the white dashed lines with bit spacings of 170 nm and 65 nm. The normalized data, $I_{norm}=I_{RF,1}/I_{RF,2}$, was plotted, to reveal magnetic field lines corresponding to a sample magnetic field along the NV axis of $B_{NV}=\pm 3$ G. Additionally, a bias magnetic field of $B_{NV} \approx 52$ G was applied to determine the sign of the measured magnetic fields. The shape of the observed domains is well reproduced by calculating the response of the NV magnetometer to an idealized sample with rectangular magnetic domains of dimensions corresponding to the written tracks.

FIG. 5B shows a similar magnetic image as in FIG. 5A, but with the NV-sample distance decreased by an estimated 50 nm. The spatial resolution of an NV magnetometer is affected by the distance from the NV centre to the sample. Bringing the NV closer to the sample increases the magnetic field magnitude at the NV sensor, and improves the imaging spatial resolution, allowing the imaging of magnetic bits, ×38 nm in width. Approaching the NV sensor more closely to the magnetic sample revealed magnetic bits with average sizes of ~28 nm, as shown in FIG. 4B. In this image, due to the large field gradients generated at the boundaries between domains, transitions between magnetic field lines could be observed on length scales of ~3 nm. Approximate NV-sample distances are noted in the schematics illustrating the experimental configuration, with the sensing NV centre fixed on the optical axis and the magnetic sample scanned below the pillar. Total image acquisition times were 11.2 min (50 ms per pixel) for FIG. 5A and 12.5 min (75 ms per pixel) for data in FIG. 5B, with laser powers of 130 µW.

Figure 5C:
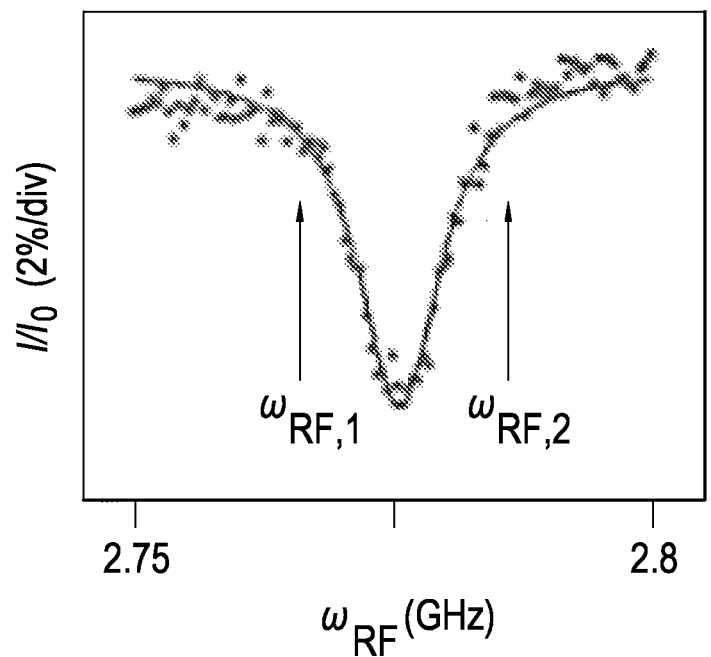
FIG. 5C shows optically detected ESR of the sensing NV centre.
Figure 5D:
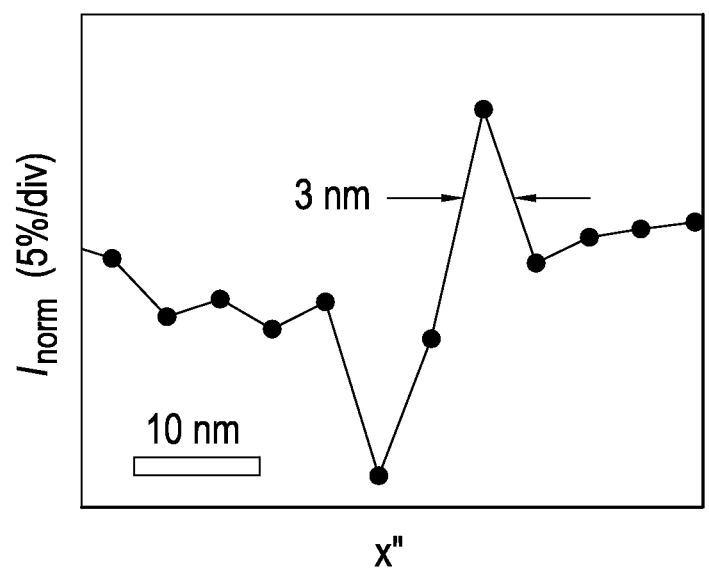
FIG. 5D is a line cut along white line shown in FIG. 5B.
Figure 5E:
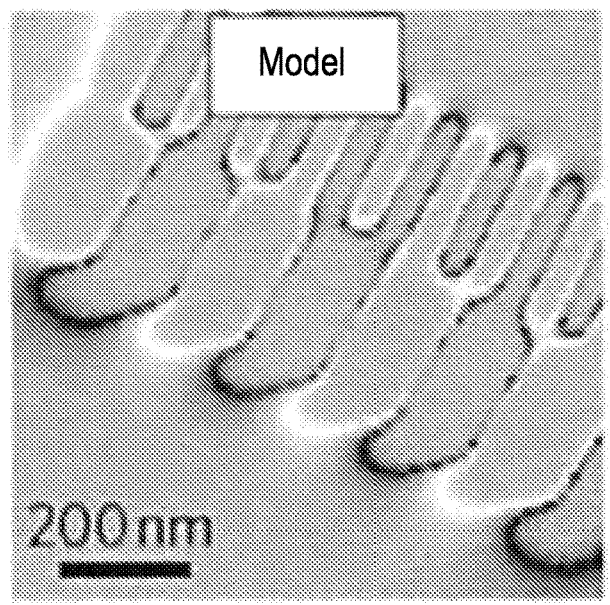
FIG. 5E shows a model calculated NV response for the experimental situation of FIG. 5A, under the assumption of a simplified magnetic sample.
Figure 5F:
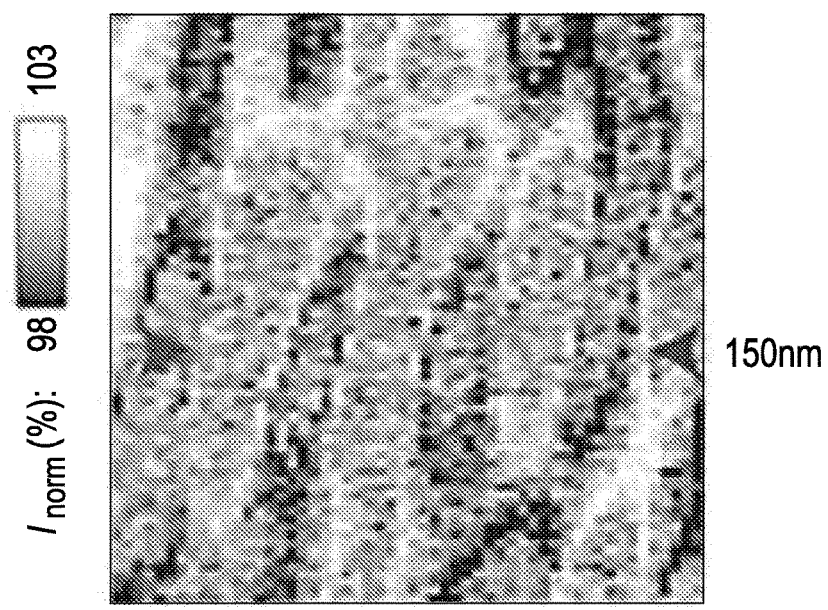
FIG. 5F illustrates magnetic images as in FIG. 5A and FIG. 5B with an experimental realization in which the smallest observed domains have average sizes of 25 nm.

FIG. 5C shows optically detected ESR of the sensing NV centre. FIG. 5D is a line cut along white line shown in FIG. 5B. FIG. 5E shows a model calculated NV response for the experimental situation of FIG. 5A, under the assumption of a simplified magnetic sample. FIG. 5F illustrates magnetic images as in FIG. 5A and FIG. 5B with an experimental realization in which the smallest observed domains have average sizes of 25 nm.

An even further decrease of NV-sample distance enables imaging of yet smaller domains, ~25 nm in width (FIG. 5F), but with a reduced imaging contrast caused by strong magnetic fields transverse to the NV axis, which occur in close vicinity to the surface of the sample. One of the disadvantages of using a hard drive to characterize the tip is that the local magnetic fields are very large and exceed the typical dynamic range of this technique. However, such experiments provide valuable information regarding NV-sample distance, and consequently the spatial resolution achieved in imaging. In particular, it is estimated that the distance between the scanning NV and the sample to be comparable to 25 nm, based on the smallest magnetic domain sizes observed.

To independently verify the proximity of the NV to the diamond surface, a measurement was conducted in which a sharp metallic tip (<20 nm in diameter) was scanned over the NV-containing pillar to image the location of the NV. The imaging contrast consisted of the detected NV fluorescence in the far-field changing when the NV was located in close proximity to the metallic tip. Owing to the strong dependence of NV fluorescence rate on the distance between the NV and the metallic sample, in this case due to partial fluorescence quenching and local modifications of excitation light intensity, this technique could be used to precisely locate the position of the NV centre within the diamond nanopillar.

Figure 6A:
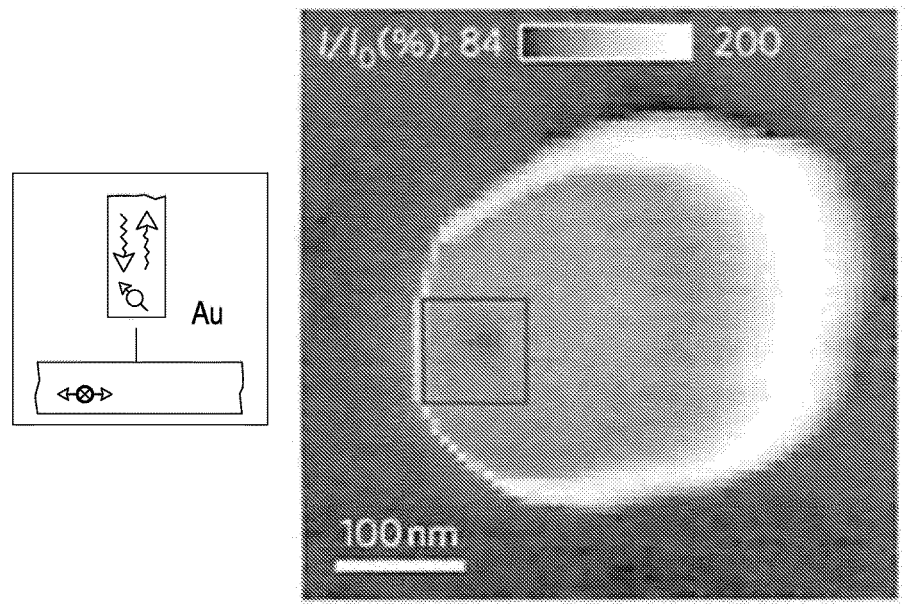
FIG. 6A is a schematic diagram of an experimental configuration for scanning of a diamond pillar over a sharp metallic tip, as well as the resulting fluorescence signal.
Figure 6B:
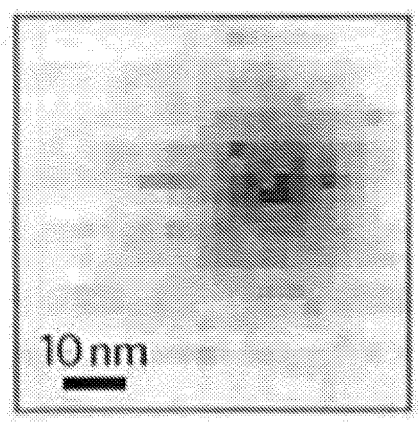
FIG. 6B shows a zoomed-in image of a red square region at the location of the NV centre.
Figure 6C:
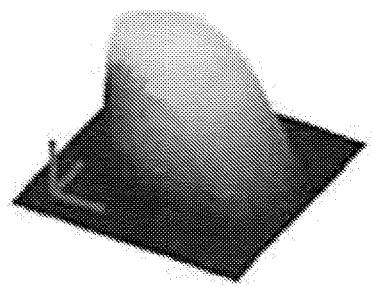
FIG. 6C is an AFM (atomic force microscopy) topography image obtained simultaneously with the data of FIG. 6B.

FIGS. 6A, 6B, and 6C illustrate nanoscale fluorescence quenching imaging of the scanning NV sensor. FIG. 6A is a schematic diagram of an experimental configuration for a scanning of the diamond pillar over a sharp metallic tip, as well as the resulting fluorescence signal. FIG. 6B shows a zoomed-in image of a red square region at the location of the NV centre. FIG. 6C is an AFM topography image obtained simultaneously with the data of FIG. 6B.

Scanning the diamond pillar over a sharp metallic tip leads to a bright, circular feature due to the sample topography. Positioning the metallic tip exactly at the location of the NV centre (shown in square), however, yields a sharp dip in NV fluorescence. The illustration shows the experimental configuration used in this experiment.

FIG. 6B is a zoomed-in image of the square region in FIG. 6A. The observed fluorescence quenching dip has a spatial resolution of ×20 nm. FIG. 6C is an AFM topography image obtained simultaneously with the data in FIG. 6B. The scale bars represent 100 nm displacement in all directions. Image acquisition times were 30 min (320 ms per pixel) and 2.7 min (250 ms per pixel) in FIG. 6A and FIG. 6B, respectively, at a laser power of 35 µw.

The resulting data showed signatures of the topography of the scanning diamond nanopillar, appearing as bright ring in the NV fluorescence signal. More importantly, however, while the front-end of the diamond probe scanned over the sharp metallic tip, a dip in NV fluorescence (square in FIG. 6A and zoomed image in FIG. 6B) was observed when the metallic tip was positioned at the location of the NV centre. This feature is not accompanied by any topographic features and is thus attributed to partial quenching of the NV fluorescence due to the sharp metallic tip. The Gaussian width (double standard deviation) of 25.8 nm of this fluorescence quenching spot was probably still limited by the size of the metallic tip and therefore marks an upper bound to the ability to localize the NV centre within the pillar. Such data allow the position of the single NV centre to be found with respect to the topography of the device. This may greatly facilitate precise alignment of the sensing NV centre with respect to targets in future sensing and imaging applications.

A remaining uncertainty to the distance between the scanning NV centre and the sample is vertical straggle in the NV implantation process. Naturally occurring stable NV centres have been observed as close as 3 nm from diamond surfaces, so future advances in the controlled creation of NV centres may allow for the NV-sample distance to be further improved and therefore the spatial resolution in scanning NV imaging by about one order of magnitude. Additionally, the coherence properties of artificially created NV centres close to the diamond surface could be further improved by annealing techniques or dynamical decoupling, which may both significantly improve the magnetic sensing capabilities of the scanning NVs. For magnetic field imaging, the ability to resolve individual magnetic domains, using the above described methods, equals the typical performance of alternative methods, with the added advantages of being non-invasive and quantitative.

FIGS. 7A, 7B, and 7C relate to the simulation of magnetic images obtained with an NV scanning sensor. FIG. 7A shows the current distribution used to simulate magnetic bits that were imaged with an NV scanning sensor, whereas FIG. 7B shows the magnetic field, projected on the NV axis, generated by the current distribution in FIG. 7A.

In order to reproduce the magnetic images obtained with the scanning NV sensor, a model-calculation of the local magnetic fields in proximity to the hard-disc sampled imaged in the experiment was performed. The magnetic domains can be approximated by an array of current-loops in the sample-plane as illustrated in FIG. 7A. The sizes of the loops can be chosen to match the nominal size of the magnetic bits on the sample, which has bit-width 200 nm and bit-length 125 nm and 50 nm for the tracks shown in the figure. The current was set to 1 mA, corresponding to a density of ≈1Bohr magneton per $(0.1 \text{ nm})^2$. These values were found to yield the best quantitative match to the magnetic field strengths observed in the experiment. Biot-Savart's law can then be applied to the current-distribution to obtain the magnetic field distribution in the half-plane above the sample.

FIG. 7B shows the resulting magnetic field projection onto the NV centre at a scan height of 50 nm above the current loops. The NV direction can be experimentally determined to be along the ([011]) crystalline direction of the diamond nanopillar, in a coordinate-system where x-, y- and z-correspond to the horizontal, vertical and out-of plane directions in FIG. 7B, by monitoring the NV-ESR response to an externally applied magnetic field. The external magnetic field may be applied using 3-axis Helmholtz-coils. Slight variations of the NV orientation due to alignment errors between the diamond crystallographic axes and the scan directions can be allowed to find the NV orientation that reproduce the experimental data best. With this procedure, the NV orientation ($\sqrt{2}$ sin ($\phi$), $\sqrt{2}$ cos($\phi$), 1)/$\sqrt{5}$, with $\phi=\pi 162/180$, was found.

This magnetic-field distribution can be used to calculate the response of the NV centre to a magnetometry scan, as described above. For this calculation, Lorentzian ESR response with a full-width at half maximum of 9.7 MHz, a visibility of 20% and two external RF sources with detunings ±10 MHz from the bare ESR frequency were assumed, in accordance with original experimental parameters.

FIGS. 8A, 8B, 8C, 8D and 8E relate to NV magnetometry in close proximity to a strongly magnetized sample.

The presence of a strong magnetic field $B_\perp$, transverse to the NV axis leads to a reduction of contrast in optically detected ESR and moreover reduces the overall fluorescence intensity of the NV centre. These effects result from a mixing of the NV spin-levels in the optical ground and excited states of the NV centre in the presence of $B_\perp$. Such mixing on one hand allows for spin non-conserving optical transitions and on the other hand suppresses the spin-dependence in shelving from the NV excited state (triplet) to the metastable NV singlet states. Both spin-conservation under optical excitation and spin-dependant shelving are responsible for the non-zero contrast in optically detected ESR of NV centres and consequently, their suppression with transverse magnetic fields explains the disappearance of NV magnetometry features when closely approaching a strongly magnetized sample.

Figure 8A:
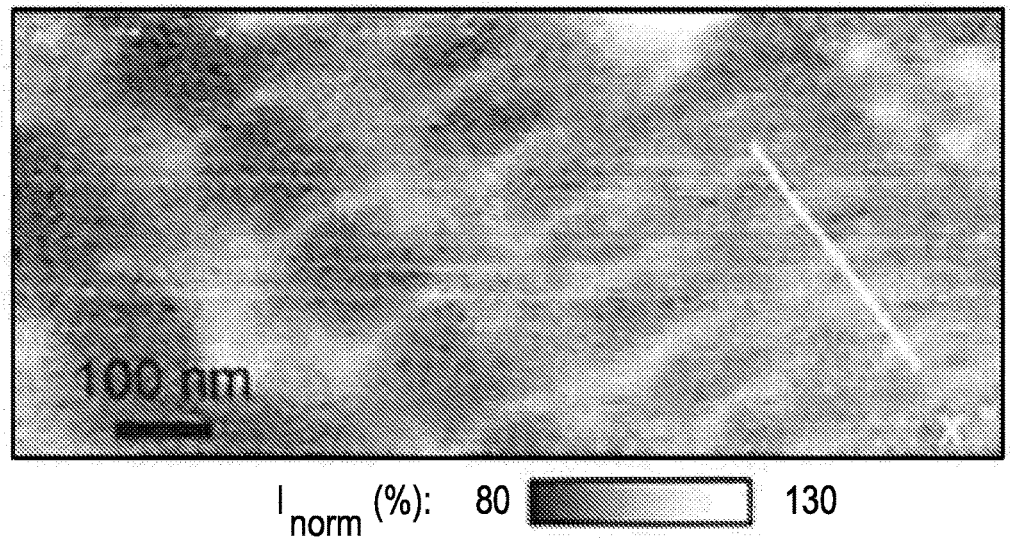
FIG. 8A shows the total NV fluorescence as a function of sample position for an NV in close proximity to the hard-disc sample.
Figure 8B:
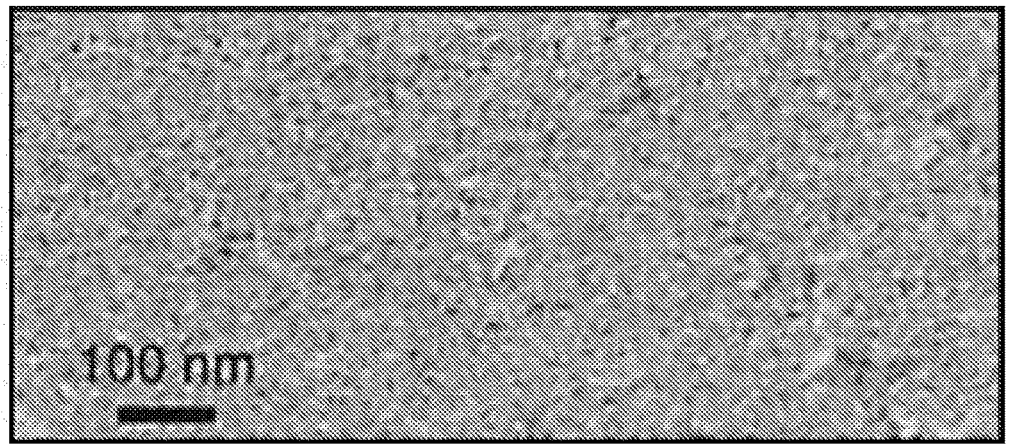
FIG. 8B shows an NV magnetic image recorded simultaneously with the NV fluorescence counts of FIG. 8A.
Figure 8C:
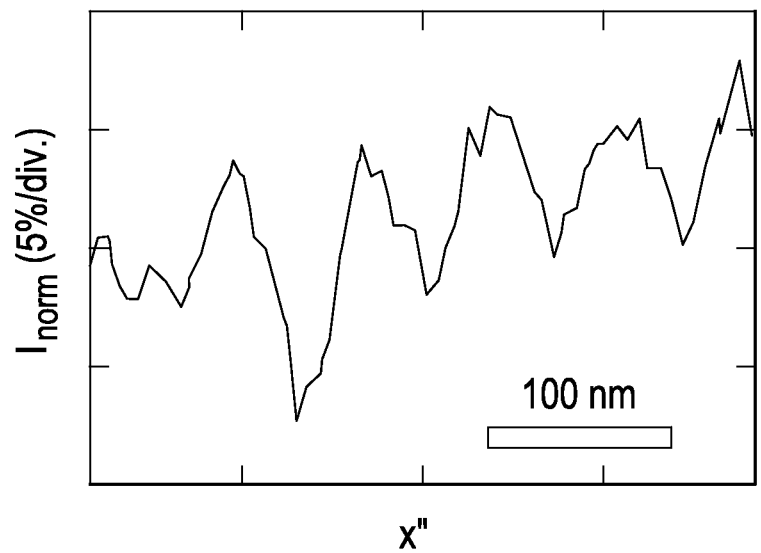
FIG. 8C shows a line cut along the white line shown in FIG. 8A, averaged over 7 adjacent pixels.

FIG. 8A shows the total NV fluorescence as a function of sample position for an NV in close proximity to the hard-disc sample, while FIG. 8B shows an NV magnetic image recorded simultaneously with the NV fluorescence counts of FIG. 8A. FIG. 8C shows a line cut along the white line shown in FIG. 8A, averaged over 7 adjacent pixels. In particular, the raw NV fluorescence counts in FIG. 8A were observed when scanning an NV in a diamond nanopillar in close proximity to the sample, at an estimated distance of 25 nm between NV and sample surface. Dark features appear when the NV is scanned over magnetic bits that enhance $B_\perp$, while the inverse happens when $B_\perp$ is reduced, or the longitudinal field $B_{NV}$ enhanced, by local fields. This mode of bit-imaging allows for spatial resolutions ≈20-30 nm, as seen in FIG. 8C.

Figure 8D:
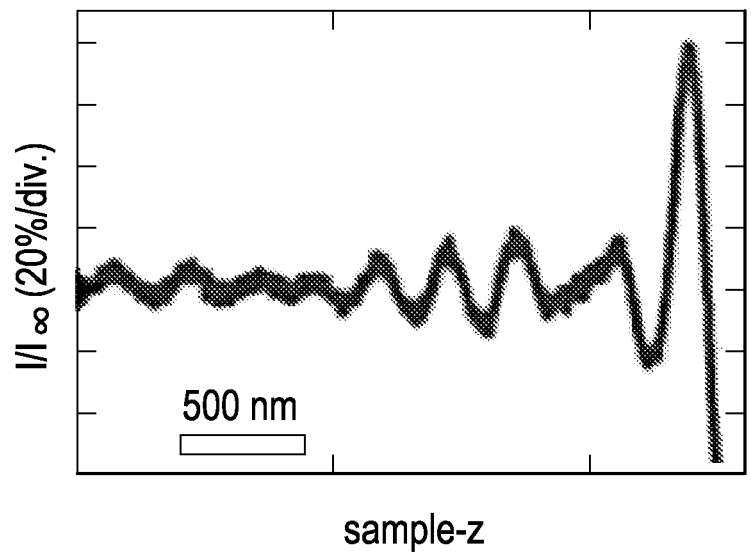
FIG. 8D is a fluorescence approach curve on the magnetic memory medium.
Figure 8E:
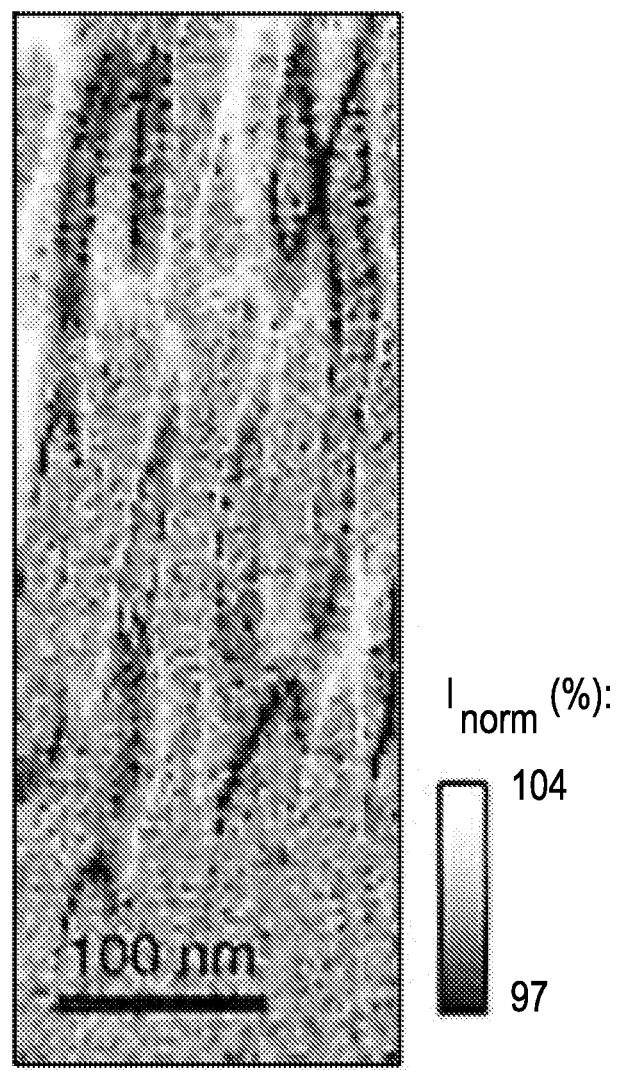
FIG. 8E shows magnetic imaging with the same NV sensor that was used for FIGS. 8A-8D, and with a same experimental realization as in FIG. 5F.

At the same time, a magnetic image recorded with the technique described in the main text shows no appreciable imaging contrast. FIG. 8D is a fluorescence approach curve on the magnetic memory medium. FIG. 8E shows magnetic imaging with the same NV sensor that was used for FIGS. 8A-8D. Only exceedingly long integration times on the order of hours would allow for weak magnetic features with dimensions on the order of 20 nm to be revealed, as seen in FIG. 8D.

The rates of the two effects which lead to a disappearance of ESR contrast, i.e. spin-flip optical transitions and shelving of $m_s=0$ electronic states into the metastable singlet, scale approximately as $$\left(\frac{B_\perp}{D_{GS} - D_{ES}}\right)^2 \text{ and } \left(\frac{B_\perp}{D_{ES}}\right)^2,$$

respectively, with $D_{GS(ES)}$ the ground-(excited-) state zero-field spin-splitting of 2.87 GHz and 1.425 GHz, respectively. Given that $D_{GS} \approx 2\ D_{ES}$, the scaling of the two mechanisms with $B_\perp$ will be very similar. The characteristic scale of $D_{ES}$ ($D_{GS}/2$) for the disappearance of ESR contrast thus allows us to estimate $B_\perp$ close to the sample to be $B_\perp D_{ES}/\gamma_{NV} \approx 514$ Gauss. However this may give an overestimation of $B_\perp$ as smaller values can already significantly affect ESR contrast and NV fluorescence intensity due to the complex dynamics of NV spin pumping. Indeed, strong reductions of NV fluorescence rates for $B_\perp$ less than 100 G have been observed in the past. Transverse magnetic fields on this order were consistent with the larges on-axis magnetic fields observed in the above experiments as well as with the calculations of magnetic field profiles described in this application. For the parameters used for these figures, maximal values of $B_1 \approx 200$ Gauss for an NV-to-sample distance of 20 nm are obtained.

NV-sample distance is an essential parameter for the performance of our microscope as it determines the overall resolving power with which weak magnetic targets can be imaged. Three parameters that can affect NV-sample distance include: depth of NV centres in the diamond nanopillars; contamination of scanning diamond nanopillars; and AFM control.

It is desirable to have NV centres controllably positioned and close to the diamond surface, for example closer than 50 nm, 40 nm, 30 nm, 20 nm, 10 nm, or 5 nm.

The depth of the NV centres created using ion implantation for example, can be controlled by the energy of the ions used for NV creation. However, the stopping of ions in matter is a random process and the depth of the created NV centres therefore not perfectly well-defined. This straggle in ion implantation poses an intrinsic uncertainty to the distance between the scanning NV and the end of the diamond nanopillar. For implantation energies of 6 keV (with implantation-depths of 10 nm) as used in this work, NV straggle has recently been shown to be as large as 10-20 nm. Since straggle in NV implantation is hard to circumvent, it is essential for the future to develop techniques to precisely pre-determine the depth of a given sensing NV in a diamond nanopillar. This could be performed using recently developed nanoscale imaging methods for NV centres, or by scanning the NV sensor over a well-defined magnetic field source.

The depth of NV centres produced through growth might be controlled by the time and duration of adding nitrogen dopant gas to the CVD diamond growth process.

Figure 9A:
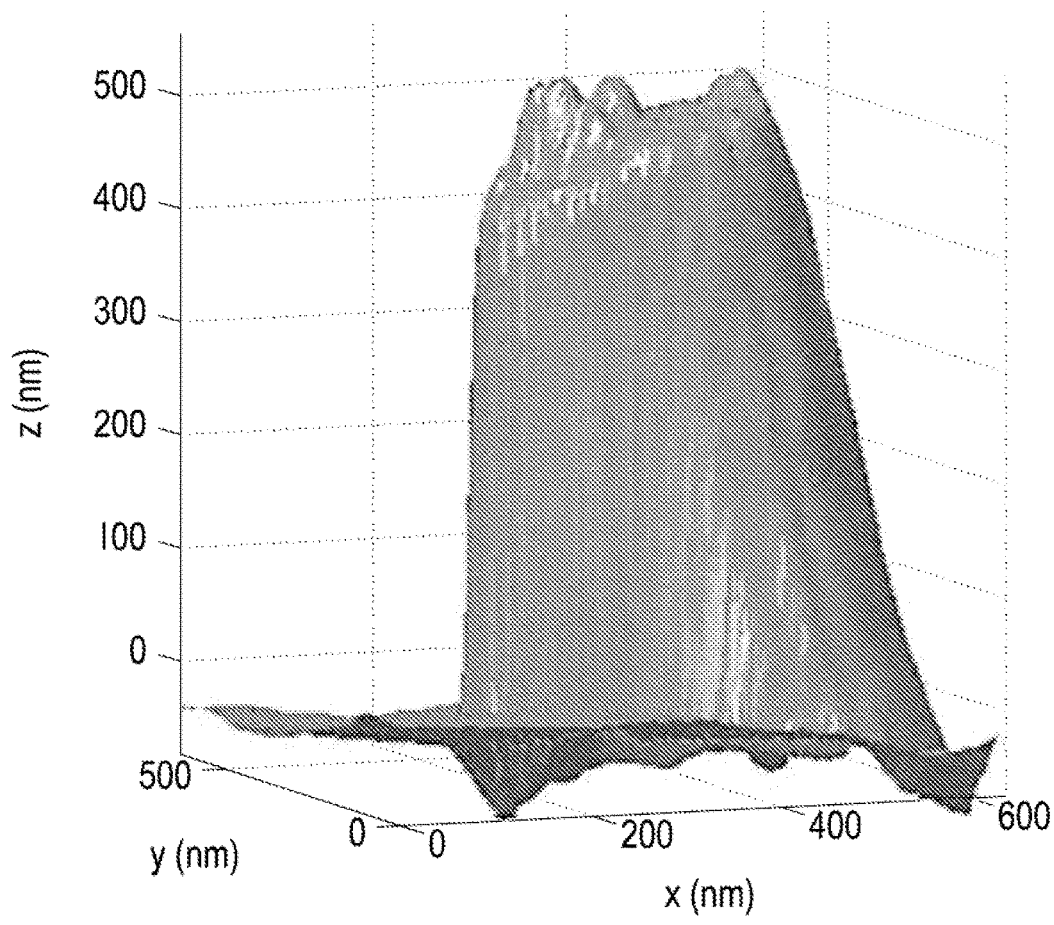
FIG. 9A is an AFM image of the end of a scanning diamond nanopillar after contamination during scanning.
Figure 9B:
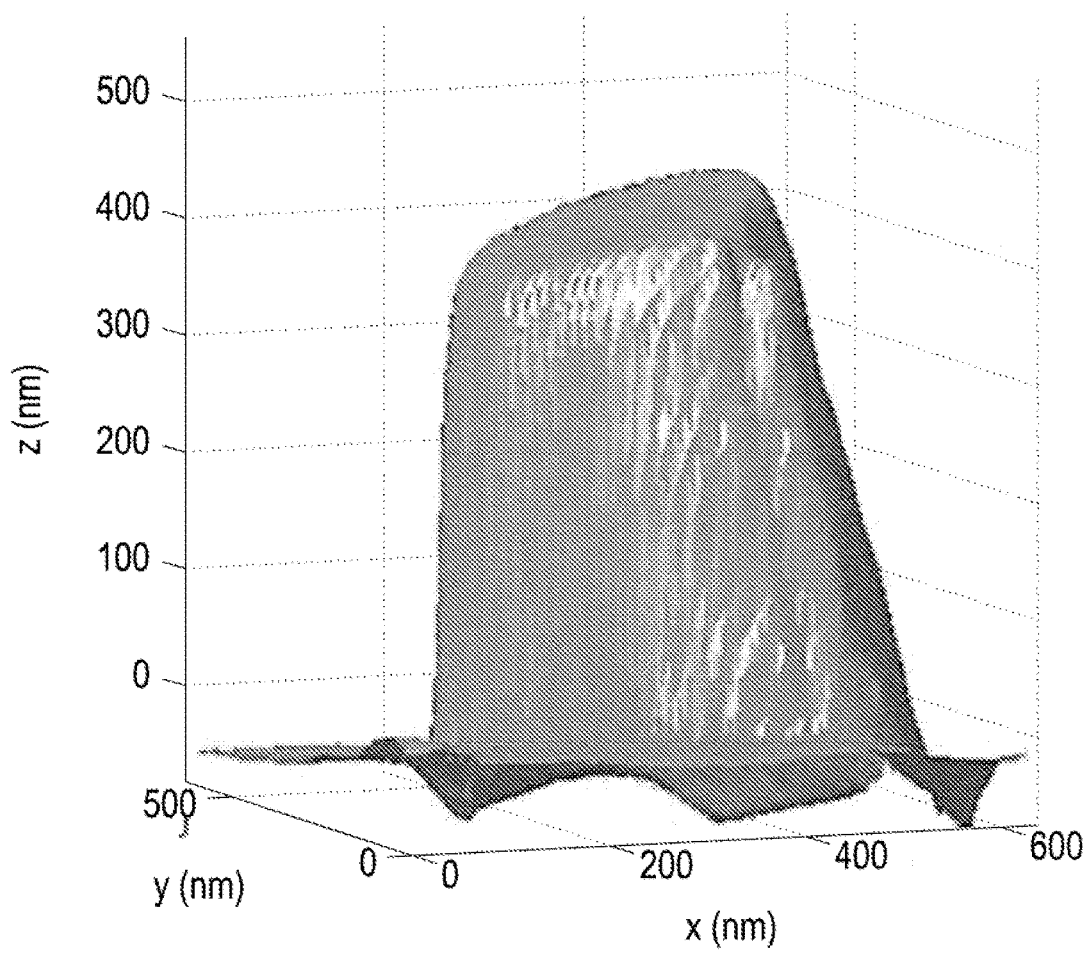
FIG. 9B is an AFM image of the same nanopillar as in FIG. 9A, after cleaning of the pillar's end face.

FIG. 9A is an AFM image of the end of a scanning diamond nanopillar after contamination during scanning FIG. 9B is an AFM image of the same nanopillar as in FIG. 9A, after cleaning of the pillar's end face.

Figure 10:
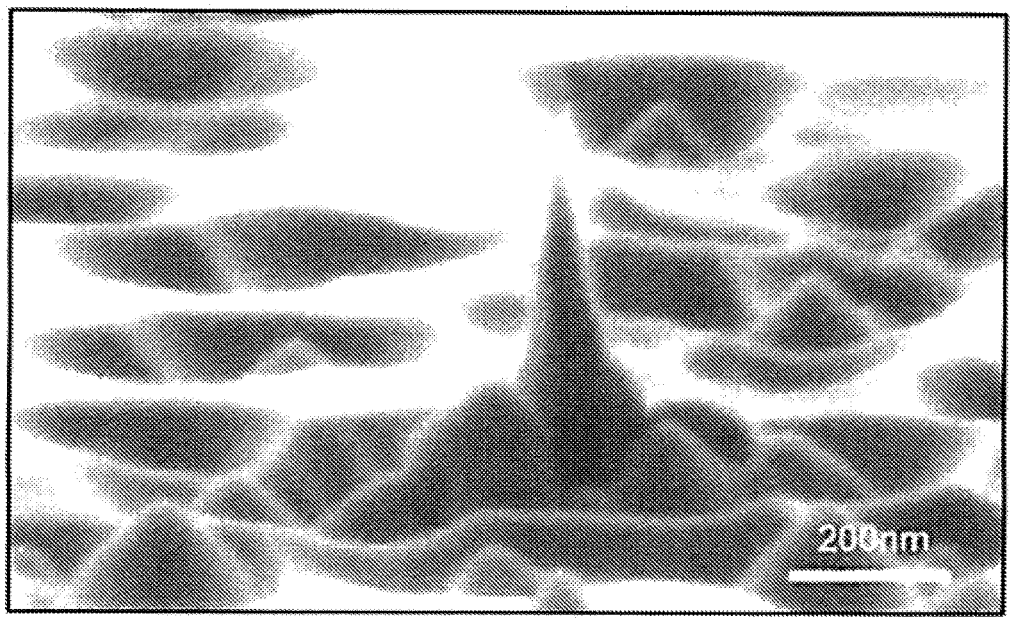
FIG. 10 is an SEM (scanning electron microscopy) image of a diamond nanopillar having a sharp pointed tip, in accordance with one or more embodiments of the present disclosure.
Figure 11C:
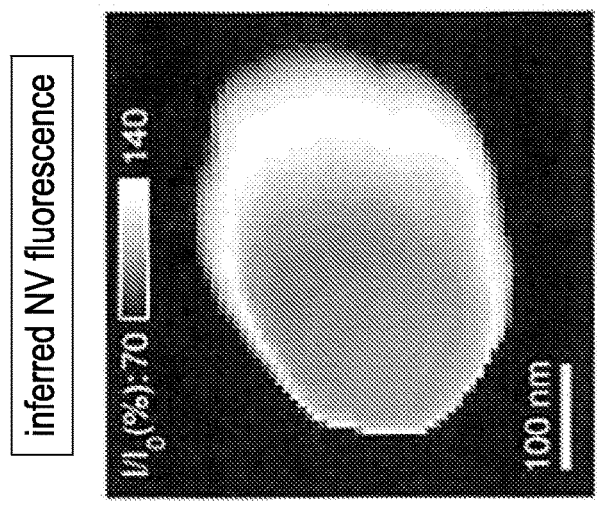
FIG. 11C shows a total fluorescence image reconstructed from the datasets taken in conjunction with FIGS. 11A and 11B.
Figure 11B:
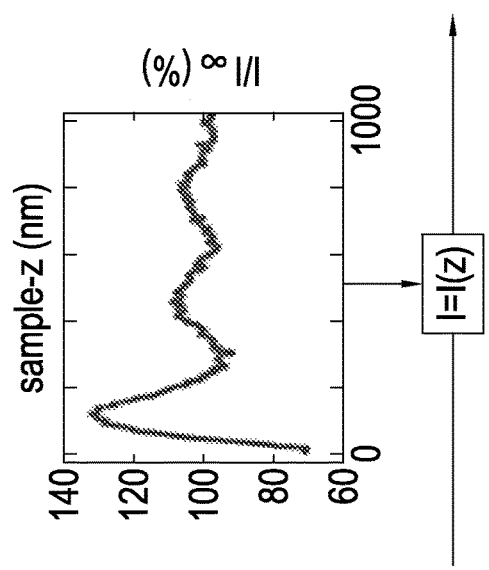
FIG. 11B illustrates an approach-curve of far-field NV fluorescence rate as the nanopillar containing the NV centre is approached to the sample.
Figure 11A:
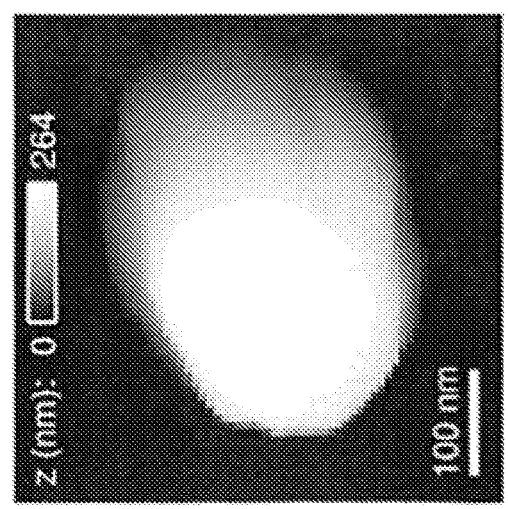
FIG. 11A illustrates AFM topography recorded during the experiment presented in FIGS. 6A-6C.
Figure 11D:
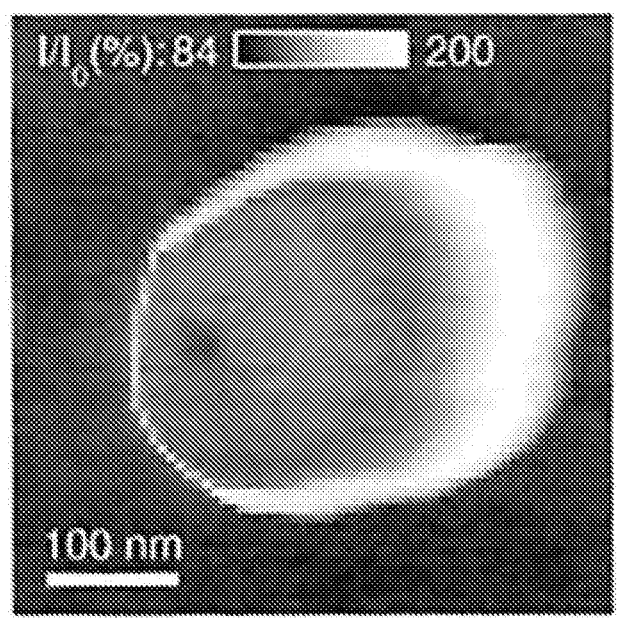
FIG. 11D illustrates measured NV fluorescence.

During scanning-operation, the scanning diamond nanopillar can gather contamination from the sample or environment. An example for such a contaminated diamond-tip is shown in the AFM image shown in FIG. 9A, which was acquired with the scanning protocol employed in FIG. 10, using a sharp diamond tip as shown in FIG. 10. Such contamination can artificially increase the distance of the scanning NV centre to the sample by several 10's of nm, as seen for example in FIG. 9A. To undo contamination of the diamond-tip after excessive scanning over dirty samples, a "tip-cleaning technique" can allow a contaminated tip to revert to its initial, clean state, as illustrated by the transition from FIG. 9A to FIG. 9B. Tip cleaning may be performed by repeated scanning of the diamond nanopillar over the sharp diamond tip (shown in FIG. 9A) in the absence of AFM feedback. Such feedback-free scanning can partly remove contamination from the diamond pillar, which after repeated operation leads to a clean device as the one shown in FIG. 9B.

With proper sample-cleaning, control over environmental conditions and occasional "tip-cleaning" runs, adverse effects of tip-contamination can be eliminated. This, together with the excellent photo-stability of NV centres, then allows for long term operation of the scanning NV sensor.

Proper AFM control is necessary to assure close proximity of the NV centre to the sample surface. It has been shown in the past that bad mounting or improper AFM feedback control can lead to AFM tip-sample distances in excess of 20 nm. Careful mounting of AFM tips and proper setup and tuning of AFM feedback, which in some embodiments may be provided by an Attocube ASC500 controller, may therefore be essential to observe e.g. the fluorescence quenching features.

For the experiment described earlier in conjunction with nanopillars with a sharp tip, sharp diamond tips were fabricated and metal coated in order to localize the NV in the scanning nanopillar through fluorescence quenching. Diamond tip fabrication was based on the nanofabrication techniques that we already employed for the production of the scanning diamond nanopillars described above. A type Ib diamond (Element six) was patterned with circular etch-masks (flowable oxide, Fox XR-1541, Dow Corning) of 100 nm diameter.

In order to obtain sharp diamond tips instead of cylindrical diamond nanopillars, the RIE etching recipe previously used can be modified: while the oxygen etching chemistry can be kept identical to pillar fabrication, the etching time can be significantly increased, such as to completely erode the etch mask on the diamond substrate. As a result, the etched diamond structures acquired the form of sharp tips as shown in the representative SEM image in FIG. 10. Typical tip-radii were in the range of 10 nm and tip lengths were on the order of 200 nm.

For the experiments described above, the sharp diamond tips were then coated with a thin metallic layer using thermal metal evaporation. To avoid oxidation of the metal, gold can be chosen as the quenching metal and a chrome adhesion can be used between the gold and the diamond. For the tips employed in this work, 5 nm of gold and 5 nm of chrome are used.

In some embodiments, one of which is illustrated in FIG. 10, diamond nanopillars that have distal ends with a sharp pointed tip 410, rather than a cylindrical cross-section, may be fabricated. In these embodiments, a diamond membrane can be patterned with circular etch-masks having a diameter on the order of about 100 nm. To obtain a sharp diamond tip, the etching time is increased significantly so as to completely erode the etch mask on the diamond membrane 414. As a result, the etched diamond structures may acquire the form of a sharp tip 410 as shown in FIG. 10.

While nanoscale scanning NV sensors have been described that use a diamond nanopillar as the scanning probe, with an individual NV centre at a small distance from a distal end of the diamond nanopillar, many other variations and embodiments are possible.

In general, a nanoscale scanning sensor system may include a solid state spin defect (for example the above-described NV centre in diamond), configured to emit fluorescent light in response to excitation light from an optical source and microwave pulses from a microwave source. The system may further include an optical outcoupling structure containing, or coupled to, the spin defect. The optical outcoupling structure may be configured to optically guide the fluorescent light emitted by the spin defect toward an output end of the optical outcoupling structure.

An optical detector may be configured to detect the fluorescent light that is emitted from the spin defect and that exits through the output end of the optical outcoupling structure after being optically guided therethrough. A mounting system (for example an AFM) may be configured to movably hold the optical outcoupling structure so as to control a distance between the spin defect and a surface of a sample while permitting relative motion between the optical outcoupling structure and the sample surface. An optical microscope may be coupled to the mounting system and configured to optically address and readout the spin defect.

The optical outcoupling structure may be movably positionable relative to the sample surface so that the sample surface can be scanned by the optical outcoupling structure while the excitation light and the microwaves are being applied to the spin defect.

In some embodiments, the optical outcoupling structure may be a single-crystal diamond membrane. In some embodiments, the optical outcoupling structure may be a diamond nanopillar as described above.

In some embodiments, the distance between the output end of the optical outcoupling structure and the spin defect may be preferably less than 50, 40, 30, 20, 10, or 5 nm.

In some embodiments, the distance between the output end of the optical outcoupling structure and the spin defect may be about 1 µm. In some embodiments, the distance between the output end of the optical outcoupling structure and the spin defect may be between 0.5 µm and 10 µm.

In some embodiments, the optical outcoupling structure may have a diameter between 100 nm and 300 nm, and a length between 0.5 µm and 5 µm.

Figure 12A:
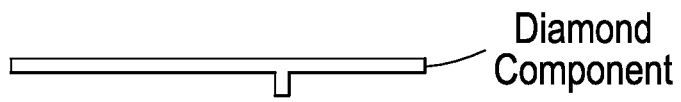
FIGS. 12A, 12B, 12C, 12D, 12E, and 12F illustrate alternative embodiments of nanosensors based on spin defects.
Figure 12B:
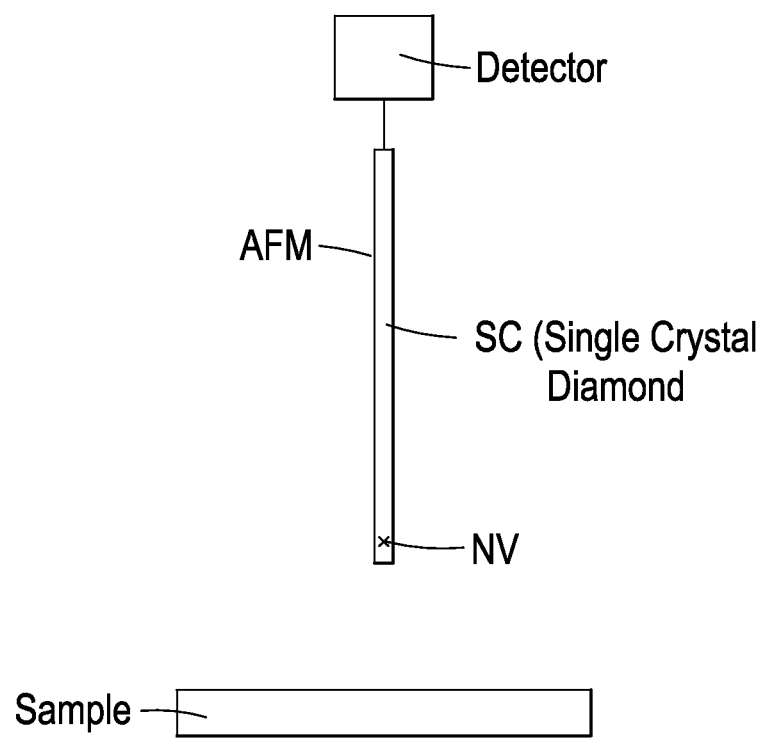

FIGS. 12A, 12B, 12C, 12D, 12E, and 12F illustrate alternative embodiments of nanosensors based on spin defects. FIG. 12A illustrates an optical outcoupling structure based on single crystal diamond. FIG. 12B illustrates an AFM-based set up as described in earlier paragraphs, but with an NV centre formed in monolithic diamond, with no nanopillar, and using total internal reflection to direct the fluorescence towards the detector.

Figure 12C:
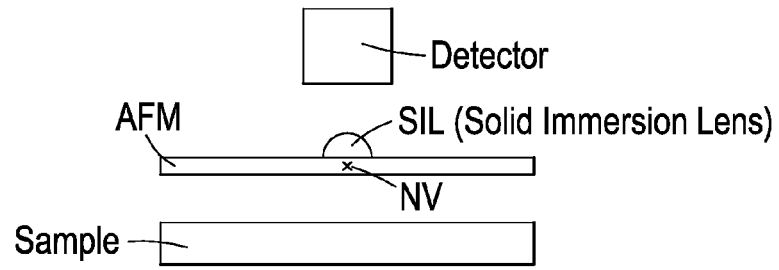
Figure 12D:
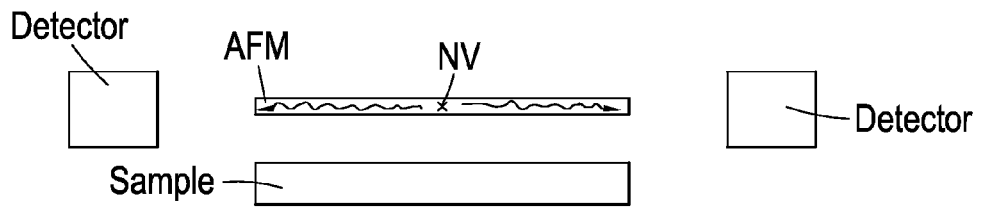
Figure 12E:
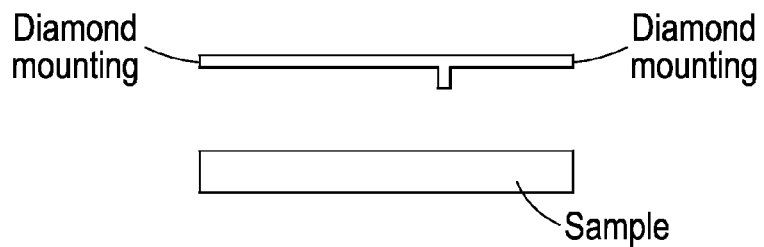
Figure 12F:
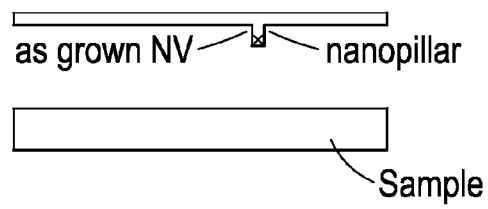

The embodiment illustrated in FIG. 12C likewise does not include a nanopillar. Rather, the optical outcoupling structure in FIG. 12C likewise is based on single crystal diamond, and includes an SIL (solid immersion lens) in the optical path of the NV centre. The SIL might be processed in the diamond, or be a separate diamond SIL attached or a SIL fabricated in another material. FIG. 12D illustrates an alternative geometry, again based on monolithic diamond and not including a nanopillar, but using total internal reflection to direct the fluorescence towards the detector. FIG. 12E illustrates a configuration in which the optical outcoupling structure can be mounted without a cantilever. In FIG. 12F, the NV centre is formed using as-grown nitrogen vacancy defects within the diamond material or nitrogen-vacancy defects formed by conversion of as-grown nitrogen into nitrogen vacancy defects by irradiation and annealing (rather than via ion-implanted nitrogen).

FIGS. 13A-13G illustrate back-etching that allows the NV distance to be further reduced. As described above, one of the most important parameters of an NV-based scanning magnetometer is the distance between the NV centre and the end of the tip of the scanning probe it is attached to.

This distance is important because it sets a lower bound for the achieved spatial resolution in magnetic imaging. Further, magnetic field strengths typically fall off rapidly with distance, so for a given magnetic sensitivity, data acquisition times fall off rapidly with decreasing distance. When measuring magnetic dipole fields, such as those from a single spin, the strength of the field falls with the cube of distance. Since the signal-to-noise of measurements goes as the square-root of integration time, the needed data acquisition time thus scales with distance to the inverse power of six ($d^{-6}$)—i.e. if the NV-to-target distance can be reduced by a factor of two, the needed integration time decreases by a factor of 64.

In order to optimize the performance of NV magnetometers, it is therefore important to minimize the distance between the NV defect and the end of scanning tip, for example the distal end (or output end) of the nanopillar. An established method for creating shallow NV centres is through nitrogen implantation and subsequent annealing. The stochastic nature of this method, however, leads to an a priori unknown NV-sample distance for a given device containing a single NV centre. Moreover, NV yield and quality fall off rapidly with implanted distance depth, and so the NV centres cannot be brought arbitrarily close to the sample surface.

In some embodiments, to achieve acceptable yields and magnetic sensitivities, nitrogen may be implanted with 6 keV energy at a dose of $3e^{11}$ N/cm$^2$. An implantation energy of 6 keV nominally forms a layer depth of 10 nm below the surface. The experimental methods described above indicate, however, an average depth of roughly 25 nm.

In some embodiments, to reduce the NV-to-sample distance a back-etching method may be used which iterates between accurately measuring the NV-to-sample distance and then carefully etching away the very end of the diamond probe. With this scheme this distance may be reduced significantly, e.g. by a factor of 2.3. Importantly, the spin properties of the NV sensor were maintained during this reduction ($T_1$, $T_2$, NV contrast, NV counts), so the NV sensitivity was preserved during the etch. Thus, the required integration time for single-spin imaging was reduced by a factor of roughly 140. The achieved single spin imaging could achieve a signal-to-noise ratio of 1 in 2 minutes of integration time. With this back-etching, the imaging may now be performed in roughly 1 second of integration time. This is an important part of this invention such that a signal to noise ratio of two for a single spin is achieved for an experimental integration of time of preferably less than 10 mins, 5 mins, 3 mins, 2 mins, 1 min, 30 seconds, 15 seconds, 10 seconds, 5 seconds, 2 seconds, 1 second, 0.5 second.

To measure the distance between the NV and the end of the scanning tip, in some embodiments a method may be used that is based on measuring the extent of fluorescence quenching into a graphene monolayer. When an optical emitter, such as an NV centre or other spin defect, is brought into close proximity of a metal (typically within tens of nanometers) instead of emitting into the optical far-field, some fluorescence is emitted into the metal, creating either plasmons or electron-hole pairs.

Typically, this fluorescence quenching changes rapidly with distance (proportional to $d^{-4}$), and so is a very sensitive measure of distance. If a graphene layer is used as the metal, because its AC conductivity is well known, the calibration between distance and the quenching amount can be quantified, which allows for a precise determination of distance. In practice, this is achieved by measuring the fluorescence from the NV centre away from a graphene flake, and then comparing how much the fluorescence decreases after it is scanned over a graphene monolayer flake. Typically the graphene flake is separated laterally, so it is still on the substrate.

With the NV-to-sample distance determined, the end of the nanopillar tip can be etched without fear of etching away the NV centre itself. In some embodiments, a process for doing this etch may be used that satisfies a few criteria: 1) The etch is slow enough to controllably etch in few (~1-3) nanometer steps; 2) The etch will not adversely influence the charge state of the NV by changing the surface termination (typically oxygen terminated); and 3) The etching process works at a low temperature, because the etch is performed after measuring the NV-to-sample distance, the NV sensor is mounted on a scanning probe which uses a series of glues that cannot survive processing above ~150 degrees Celsius.

In some embodiments, this process uses a weak oxygen plasma. FIG. 13A illustrates reducing of the NV distance via oxygen plasma. The RF power may be about 100 W, or in other alternatively may be in the range of 50-150 W, with a low-bias power. The low-bias power may be <50 W. In some embodiments, the low-bias power may be 0 W.

Figure 13B:
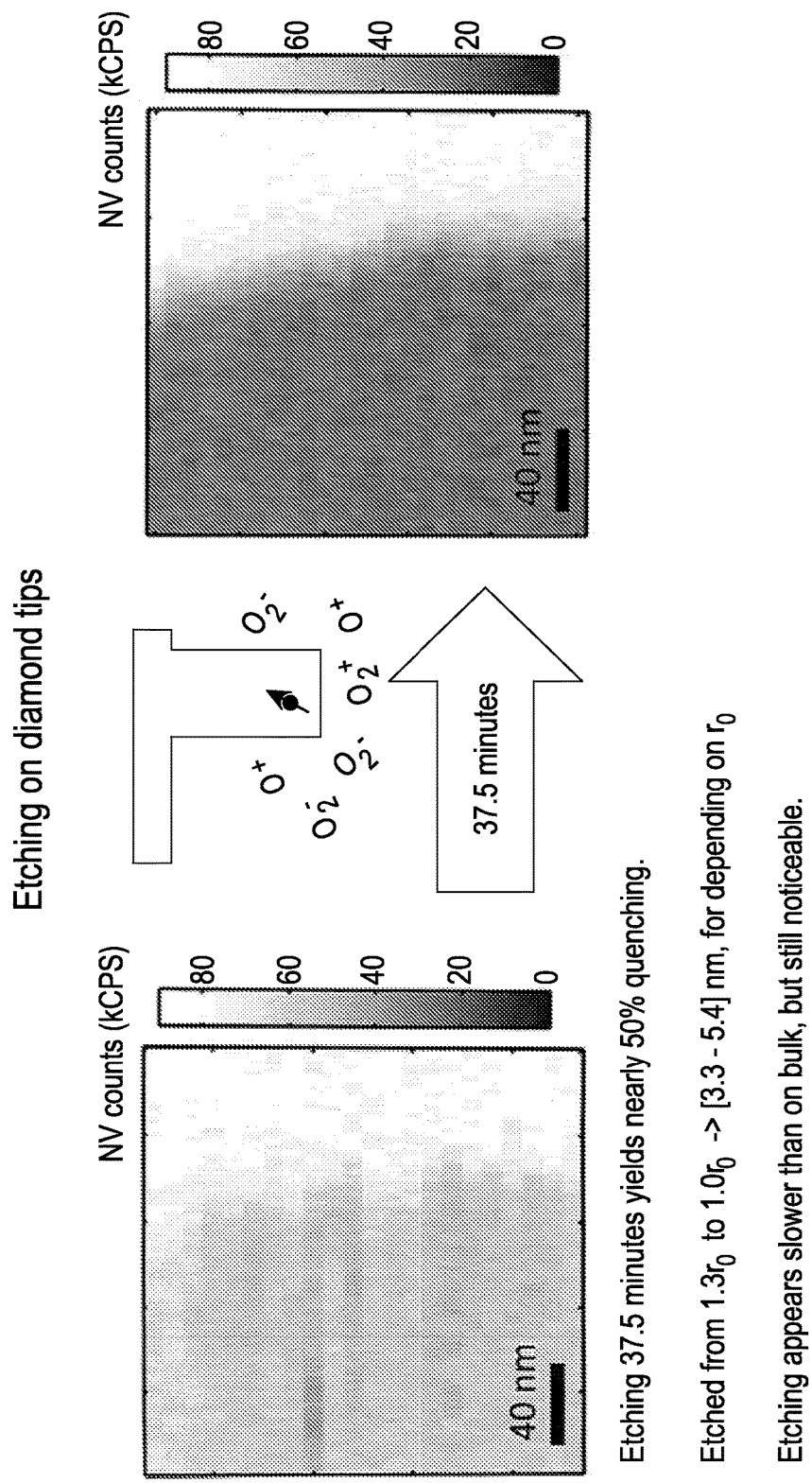
Figure 13C:
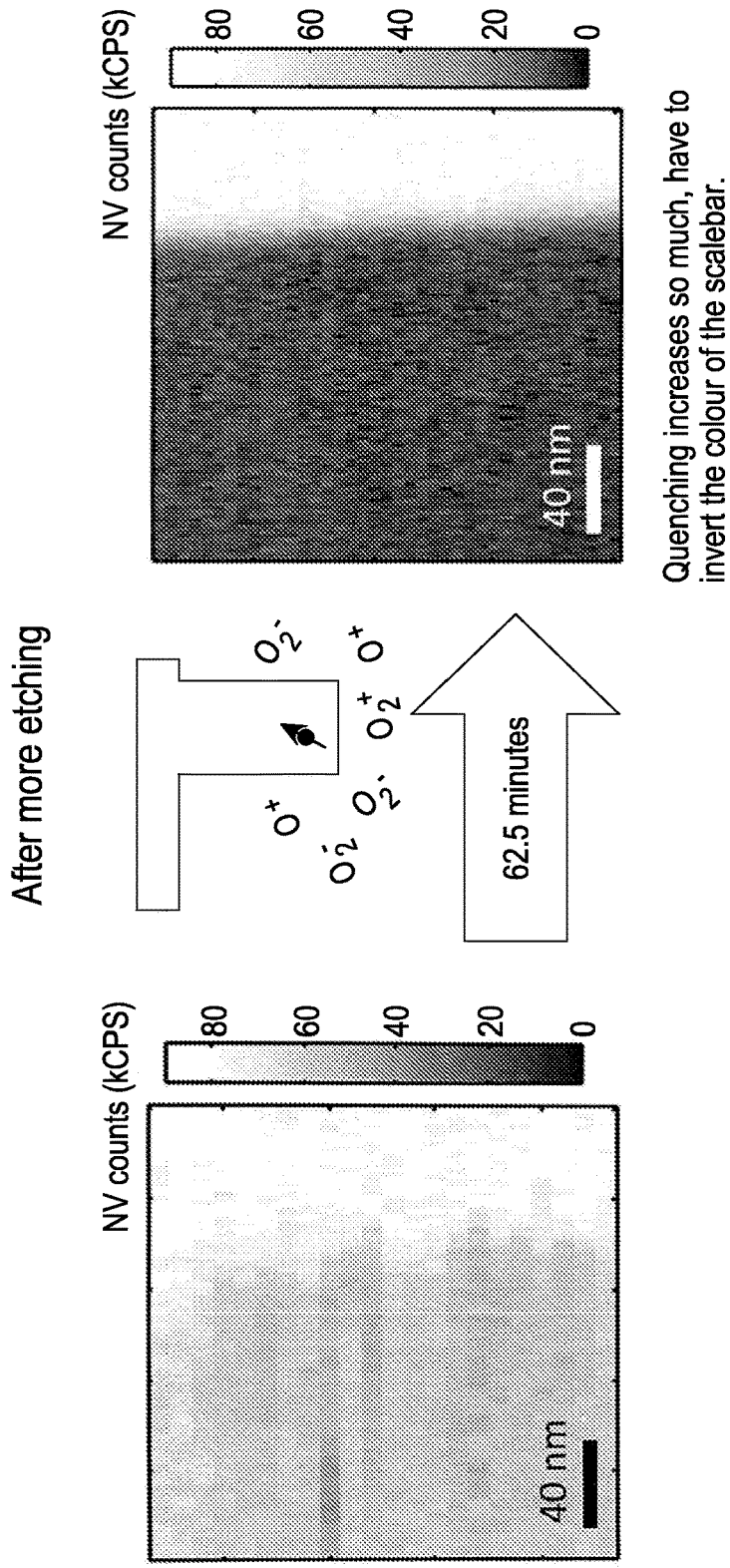

FIG. 13B illustrates etching on diamond tips. As indicated in FIG. 13B, etching 37.5 minutes yields nearly 50% quenching. The above-described etch process may be performed for up to ~20 minutes at a time. Longer times may generate excess heating, which may melt the glues that are used. FIG. 13C illustrates quenching increase after more etching. In some embodiments, etch rates of <1 nm/minute may be achieved. These etch rates may be calibrated by etching a region of diamond, partially covered by an etch mask, and then measuring the resulting diamond profile with an AFM. In some embodiments, the machine used for doing the etching may be a Plasma stripper.

Figure 13D:
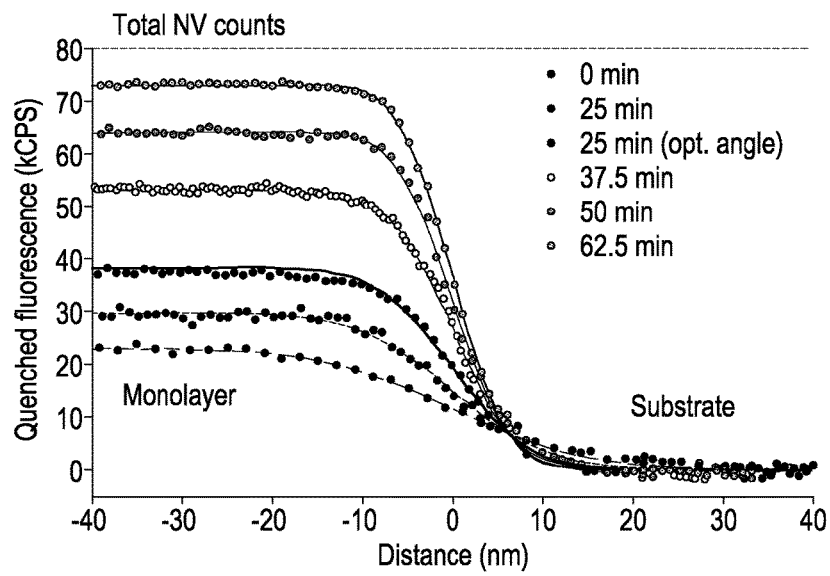
Figure 13E:
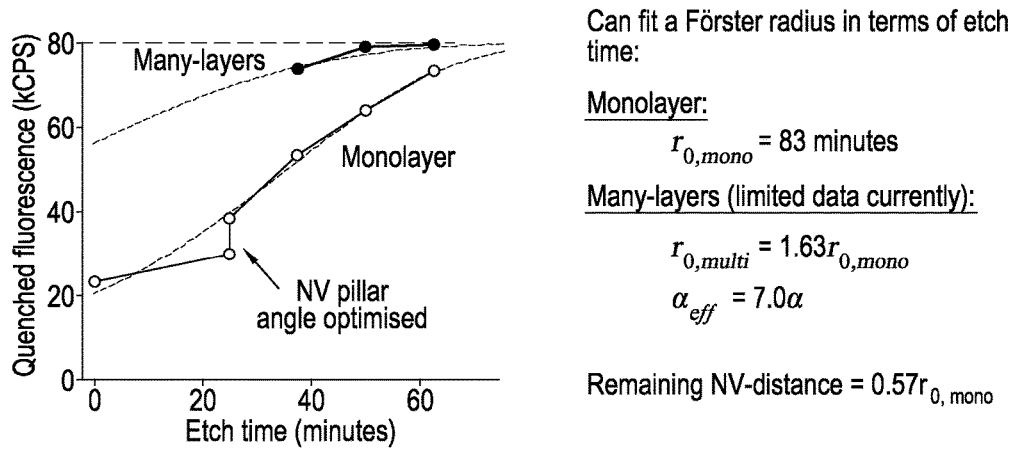
Figure 13F:
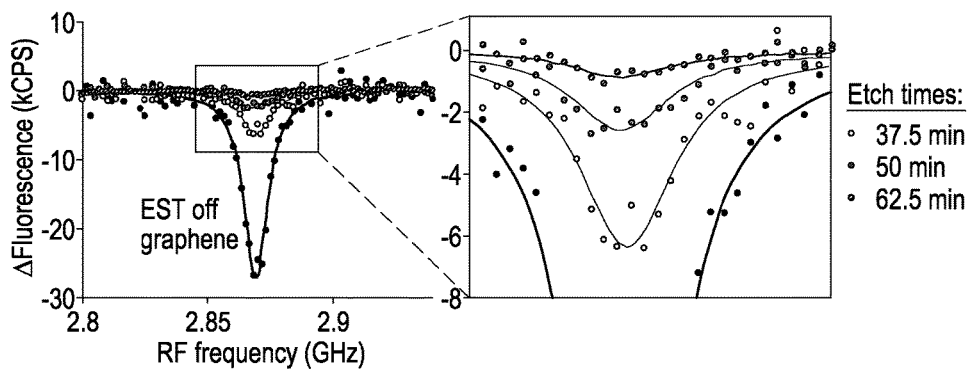
Figure 13G:
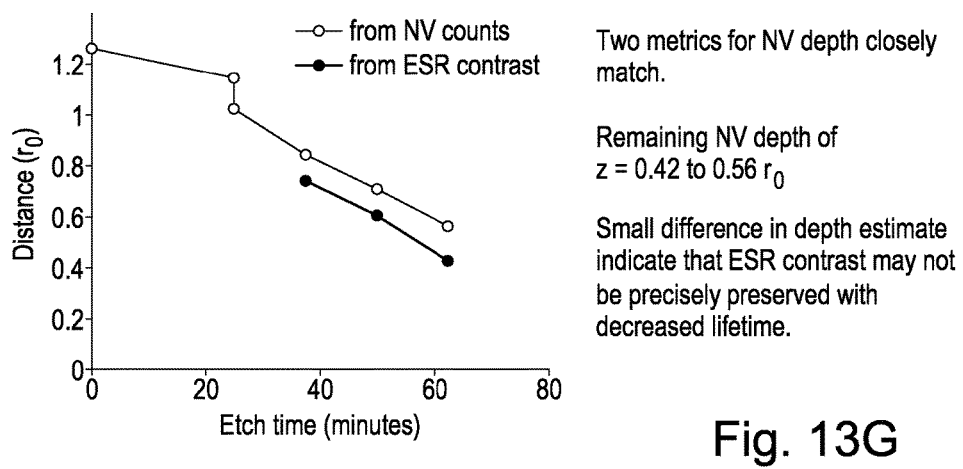

FIG. 13D illustrates graphene quenching vs. etch time, while FIG. 13E illustrates NV fluorescence v. etch time. FIG. 13F illustrates the ESR counts for confirming NV distance. A summary of NV depth v. etch time is provided in FIG. 13G.

In summary, methods and systems have been described relating to nanoscale scanning sensors with spin defects, such as single NV centres. These sensors achieve long spin coherence times, together with high mechanical robustness and high signal collection efficiencies The methods and systems described above has many other potential applications. These applications include without limitation optical sensors, as well as platforms for coherently coupling the scanning NV spin to other spin systems such as phosphorus in silicon, other NV centres, or carbon-based spin qubits. Quantum information could thereby be transferred between a stationary qubit and the scanning NV centre described above, and from there to single photons or other qubit systems such as long-lived nuclear spin qubits in the diamond matrix.

The components, steps, features, objects, benefits and advantages that have been discussed are merely illustrative. None of them, nor the discussions relating to them, are intended to limit the scope of protection in any way. Numerous other embodiments are also contemplated, including embodiments that have fewer, additional, and/or different components, steps, features, objects, benefits and advantages. The components and steps may also be arranged and ordered differently.

Nothing that has been stated or illustrated is intended to cause a dedication of any component, step, feature, object, benefit, advantage, or equivalent to the public. While the specification describes particular embodiments of the present disclosure, those of ordinary skill can devise variations of the present disclosure without departing from the inventive concepts disclosed in the disclosure.

While certain embodiments have been described, it is to be understood that the concepts implicit in these embodiments may be used in other embodiments as well. In the present disclosure, reference to an element in the singular is not intended to mean "one and only one" unless specifically so stated, but rather "one or more." All structural and functional equivalents to the elements of the various embodiments described throughout this disclosure, known or later come to be known to those of ordinary skill in the art, are expressly incorporated herein by reference.

What is claimed:

1. A method of forming a sensing probe formed of a diamond material, the method comprising:
   providing a diamond material comprising one or more spin defects configured to emit fluorescent light; and
   forming an optical outcoupling structure formed by the diamond material and etched by a weak oxygen plasma etch, the optical outcoupling structure configured to optically guide the fluorescent light emitted by the one or more spin defects toward an output end of the optical outcoupling structure, wherein the weak oxygen plasma etch is at an etching temperature less than 150 degrees Celsius and at an RF power less than 150 W, so that the one or more spin defects are located no more than 50 nm from a sensing surface of the sensing probe, and a decoherence time of the one or more spin defects is greater than 10 µsec; and
   wherein the sensing probe including the optical outcoupling structure is formed of a diamond component having at least one linear dimension greater than 1 µm in length.

2. The method of claim 1, wherein the one or more spin defects are located no more than 40 nm, 30 nm, 20 nm, 15 nm, 12 nm, or 10 nm from the sensing surface of the sensing probe.

3. The method of claim 1, wherein the one or more spin defects are NV⁻ (nitrogen-vacancy) defects.

4. The method of claim 1, comprising forming the sensing probe including the optical component of a single crystal diamond material.

5. The method of claim 1, wherein a decoherence time of the one or more spin defects is greater than 10 µsec, 50 µsec, 100 µsec, 200 µsec, 300 µsec, 500 µsec, or 700 µsec.

6. The method of claim 1, comprising forming the optical outcoupling structure by any one of a nanopillar; an immersion lens, and via internal reflection.

7. The method of claim 6, wherein the optical outcoupling structure is formed of a nanopillar.

8. The method of claim 7, wherein the nanopillar has a diameter between 100 nm and 300 nm, and a length between 0.5 µm and 5 µm.

9. The method of claim 1, wherein the sensing probe comprises no more than 50, 30, 10, 5, 3, 2, or 1 spin defects located no more than 50 nm from the sensing surface and optically coupled to the optical outcoupling structure.

10. The method of claim 1, wherein the sensing probe comprises more than 50 spin defects in the form of a layer located no more than 50 nm from the sensing surface and optically coupled to the optical outcoupling structure.

* * * * *